US011104859B2

(12) United States Patent
Isbell et al.

(10) Patent No.: US 11,104,859 B2
(45) Date of Patent: Aug. 31, 2021

(54) POLYETHYLENE DIESTER VISCOSITY MODIFIERS

(71) Applicant: The United States of America, as represented by the Secretary of Agriculture, Washington, DC (US)

(72) Inventors: Terry Isbell, Elmwood, IL (US); Steven C. Cermak, Galesburg, IL (US); Benjamin A. Lowery, Bartonville, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 11 days.

(21) Appl. No.: 16/538,148

(22) Filed: Aug. 12, 2019

(65) Prior Publication Data

US 2021/0047580 A1 Feb. 18, 2021

(51) Int. Cl.
*C10M 145/38* (2006.01)
*C07C 67/04* (2006.01)
*C10N 30/02* (2006.01)

(52) U.S. Cl.
CPC .......... *C10M 145/38* (2013.01); *C07C 67/04* (2013.01); *C10M 2203/1025* (2013.01);
(Continued)

(58) Field of Classification Search
CPC .......... C10M 145/38; C10M 2209/109; C10M 129/78; C10M 2203/1025;
(Continued)

(56) References Cited

U.S. PATENT DOCUMENTS

2003/0101641 A1\* 6/2003 Mathur ............... C10L 1/10
44/308
2004/0137025 A1\* 7/2004 Kosugi ............... A61Q 1/02
424/401
(Continued)

FOREIGN PATENT DOCUMENTS

GB 640464 A \* 7/1950 ............... B01B 1/04
GB 727667 A \* 4/1955 ............... C10M 1/08
GB 874550 A \* 8/1961 ......... B01D 19/0404

OTHER PUBLICATIONS

Greco-Duarte, J., Cavalcanti-Oliveira, E.D., Da Silva, J.A.C., Fernandez-Lafuente, R., Freire, D.M.G., "Two-step enzymatic production of environmentally friendly biolubricants using castor oil: Enzyme selection and product characterization", Fuel, 2017, p. 196-205 (Year: 2017).\*

*Primary Examiner* — James C Goloboy
(74) *Attorney, Agent, or Firm* — John D. Fado; G. Byron Stover

(57) ABSTRACT

Disclosed are compositions containing at least one of the following:
(1) estolide polyethylene glycol diesters;
(2) hydroxy derived estolide polyethylene glycol diesters;
(3) unsaturated hydroxy derived estolide polyethylene glycol diesters;
(4) estolide trimetholpropane diesters;
(5) hydroxy derived estolide trimetholpropane diesters;
(6) unsaturated hydroxy derived estolide trimetholpropane diesters;
(7) estolide epoxide polyethylene glycol diesters;
(8) estolide dihydroxide polyethylene glycol diesters;
(9) mono-capped hydroxy derived estolide epoxide polyethylene glycol diesters;
(10) mono-capped hydroxy derived estolide dihydroxide polyethylene glycol diesters;
(Continued)

and mixtures thereof; and optionally a carrier. All the compounds can be used as a viscosity index improver thereby improving a lubricant's performance.

6 Claims, 6 Drawing Sheets

(52) U.S. Cl.
CPC .............. *C10M 2205/0285* (2013.01); *C10M 2209/109* (2013.01); *C10N 2030/02* (2013.01)

(58) Field of Classification Search
CPC ...... C10M 2205/0285; C10M 2207/30; C01N 2030/02; C01N 2020/02; C07C 67/04
See application file for complete search history.

(56) References Cited

U.S. PATENT DOCUMENTS

| | | | | |
|---|---|---|---|---|
| 2007/0166270 | A1* | 7/2007 | Neuss | A61K 8/8152 424/70.31 |
| 2008/0051303 | A1* | 2/2008 | Brand | C08K 5/103 508/100 |

* cited by examiner

POLYETHYLENE DIESTER VISCOSITY MODIFIERS

BACKGROUND OF THE INVENTION

Disclosed are compositions containing at least one of the following:
(1) estolide polyethylene glycol diesters;
(2) hydroxy derived estolide polyethylene glycol diesters;
(3) unsaturated hydroxy derived estolide polyethylene glycol diesters;
(4) estolide trimetholpropane diesters;
(5) hydroxy derived estolide trimetholpropane diesters;
(6) unsaturated hydroxy derived estolide trimetholpropane diesters;
(7) estolide epoxide polyethylene glycol diesters;
(8) estolide dihydroxide polyethylene glycol diesters;
(9) mono-capped hydroxy derived estolide epoxide polyethylene glycol diesters;
(10) mono-capped hydroxy derived estolide dihydroxide polyethylene glycol diesters;
and mixtures thereof; and optionally a carrier. All the compounds can be used as a viscosity index improver thereby improving a lubricant's performance. Also disclosed are methods to improve the viscosity index of a lubricant (e.g., mineral or polyalphaolefin (synthetic) base oils) involving mixing the composition with a lubricant.

Vegetable oils offer a wide range of functionality that can be utilized to make lubricants and lubricant additives by derivatization of the ester, alcohol, or olefin moieties (Karmakar, G., et al., Lubricants, 44: 1-17 (2017)). The hydroxyl containing triglycerides of castor and *lesquerella* offer all these functionalities within one molecule and, as a result, lithium soaps have all been synthesized from these starting materials (García-Zapateiro, L. A., et al., Ind. Crop Prod., 54: 115-121 (2014)), estolides (Bredsguard, J., 2017, U.S. Pat. No. 9,650,328; Bredsguard, J., and J. Forest, 2017, U.S. Pat. No. 9,605,231; Bredsguard, J., et al., 2018, U.S. Pat. No. 9,878,973; Bredsguard, J., and T. Thompson, 2013, U.S. Patent App. Pub. 2013/0324754; Cermak, S. C., et al., Ind. Crop Prod., 23: 54-64 (2006); Garcia-Zapateiro, L. A., et al., Grasas y Acetias, 61: 171-174 (2010); Forest, J., 2017, U.S. Pat. No. 9,648,892; Forest, J., et al., 2017, U.S. Pat. No. 9,840,606; Isbell, T. A., and S. C. Cermak, J. Am. Oil Chem. Soc., 79: 1227-1233 (2002); Kamalakar, K., et al., J. Oleo Sci., 64: 1283-1295 (2015); Sammaiah, A., et al., Eur. J. Lipid Sci. Technol., 118: 486-49 (2016); Thompson, T., et al., 2017, U.S. Patent App. Pub. 2017/0073601) and epoxides (Doll, K. M., et al., Ind. Crop Prod., 104: 269-277 (2017): Hernandez, N. L. P., et al., J. Mol. Cat. A: Chem., 426: 550-556 (2017)). The lithium soaps have been heavily used in grease formulations (Garcia-Zapateiro, L. A., et al., 2014) and there are reported examples containing estolides (Fish, G., et al., 2014, Environmentally Considerate Lubricants: Understanding component requirements for formulating high performance environmentally acceptable grease, ASTM International, West Conshohocken, Pa., 24-35). Estolides from castor fatty acids have been used as thickeners in lubricants (Lawate, S. S., 1995, U.S. Pat. No. 5,427,704) and as precursors to drying oils (Penoyer C. E., et al., J. Am. Oil Chem. Soc., 31: 366-370 (1954)). Esters of fatty acids have been used as lubricant base stocks and their epoxides in the coatings industry (Pelletier, H., Eur. J. Lipid Sci., 108: 411-420 (2006)). A building interest in estolides and estolide derivatives resulted in research yielding normal and branched chain esters from the residual carboxylic acid functionality and, more recently, the synthesis of a carbonate derivative from the capping fatty acid of the estolide, increasing the range of physical properties this class of lipids provides (Isbell, T. A., Grasas Y Aceites, 62: 8-20 (2011); Isbell, T. A., et al., Ind. Crop Prod., 13: 11-20 (2001); Cermak, S. C., et al., Ind. Crop Prod., 74: 171-177 (2015); Doll, K. M., et al., Ind. Crop Prod., 104: 269-277 (2017)). Alkyl and branched diesters of the estolides have been reported and this simple derivative doubles the molecular weight of the molecule and provides a large increase in the kinematic viscosity (Harry-O'kuru, R. E., et al., J. Am. Oil Chem. Soc., 78: 219-222 (2001)). No reports of diesters of estolides with polyethylene glycol (PEG) are known. In addition, a recent report demonstrated that the epoxidation of the residual olefin within the estolide is possible (Doll et al., 2017). This epoxide functionality was converted to a carbonate but epoxides hydrolyzed to dihydroxyl moieties were not studied.

Herein we report the synthesis and characterization of PEG diesters of estolides and the ability to further functionalize the residual olefin of ricinoleate with an epoxide and subsequent ring opening to a dihydroxide, yet leaving the estolide moiety intact.

Viscosity modifiers and viscosity index improvers are additives in mineral oils or synthetic base stocks that improve the viscosity performance of the oil (Martini, A., et al., Tribology Letters, 66: 58 (2018)). The goal of the lubricant is to provide a boundary layer separation between two moving metal surfaces. The oil must be of sufficient low viscosity to pass into the contact area yet be viscous enough to provide separation between the moving surfaces at all operating temperatures. Multi-grade oils that blend low and high viscosity oils work across a wider temperature range and help address this requirement. However, the desire to improve fuel economy in vehicles has required the use of a viscosity modifier in lower viscosity oils which provide less resistance to moving parts at low temperature yet still viscous enough to perform at high operating temperatures. Current viscosity modifiers are composed of polymers like styrene-butadiene copolymer, styrene-ethylene-propylene copolymer, ethylene-propylene copolymer, and polyalkylmethacrylate (Ramasamy, U.S., et al., Tribol. Lett., 65:147 (2017); Jukic, A., et al., Lubri. Sci., 17:431-449 (2005); Warren, M. J., and A. F. A. Asfour, J. Syth. Lubr., 22:249-258 (2005); Savoji, M. T., et al., Ind. Eng. Chem., 57:1840-1850 (2018)). The proposed mechanism for increasing the viscosity index of polyalkylmethacrylate modifiers is based on the solvent effect of the base oil on the polymer additive (Selby, T. W., ASLE Trans, 1:68-81 (1958); Muller, H. G., Tribology Int., June 189-192, 1978). At low temperature, the macromolecule is poorly soluble in the base oil and the polymer chains are tightly packed on one another. As the temperature increases, the solubility of the macromolecule increases and this interaction of the polymer chains with the base oil causes the polymer chains to extend throughout the solution, thereby increasing its volume and intermolecular interactions between polymer and base oil, subsequently increasing the viscosity of the solution. The olefinic copolymer class has been shown to not undergo expansion with increased temperature as the polymethacrylate copolymers but rather it is proposed to have associated entanglements with other macromolecules within the solution contributing to its viscosity index improvement properties (Martini et al. 2018).

The high molecular weight for polyalkylmethacrylate (169,600 g/mole) and olefin copolymers (304,100 g/mole) additives over time suffer from their large size where scission of the polymer chains occurs under shear stress and eventual breakdown in viscosity performance (Warren and Asfour 2005). Considerable research has been conducted on developing green lubricants over the past two decades but this effort has been focused on replacement of base oils with little effort directed toward developing renewable additives for viscosity improvement of synthetic or mineral oils (Karmaker, G., et al., Lubricants, 5: 44 (2017)). One renewable material that has received strong research interest and development is estolides derived from vegetable oil fatty acids like oleic or hydroxy fatty oils which have demonstrated good performance as base oil materials (Isbell 2011; Cermak et al. 2006; Isbell, T. A., and S. C. Cermak, J. Am. Oil Chem. Soc., 79: 1227-1233 (2002)). To extend the potential uses of estolides, we postulated that admixtures of polyethylene glycol (PEG) diesters of estolides in mineral and synthetic base oils would demonstrate reduced solubility of the additive in the base oil, and that the folding of the estolide molecule upon itself at low temperatures and unfolding at higher temperatures where its solubility increases, will surprisingly cause increased solution viscosity and a higher viscosity index (VI) of the petroleum derived base oils.

SUMMARY OF THE INVENTION

Disclosed are compositions containing at least one of the following:
(1) estolide polyethylene (PEG) glycol diesters

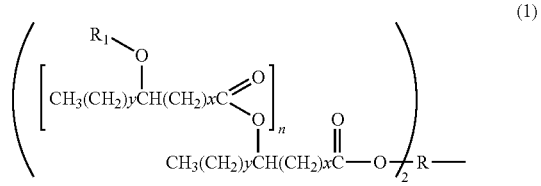

wherein x and y are each equal to 1 or greater than 1,
wherein x+y=from 11 to 21;
wherein n is 0, 1, or greater than 1;
wherein R is a residual of a diol, wherein the diol may be any chain length of polyethylene glycol;
wherein R is a triol;
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;
wherein the predominant species of secondary ester linkage is at the 9 or 10 position, or secondary ester linkage is at the 11 or 12 position, or secondary ester linkage is at the 13 or 14 position, or secondary ester linkage is at the 5 or 6 position, or secondary ester linkage is at the 12 position, or secondary ester linkage is at the 14 position;
(2) hydroxy derived estolide polyethylene glycol diesters:

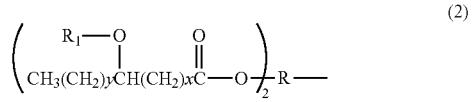

wherein x and y are each equal to 1 or greater than 1,
wherein x+y=from 11 to 21;
wherein R is a residual of a diol, wherein the diol may be any chain length of polyethylene glycol ($-CH_2-O-$);
wherein R is a residual of a triol;
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;
wherein the predominant species of secondary ester linkage is at the 9 or 10 position, or secondary ester linkage is at the 11 or 12 position, or secondary ester linkage is at the 13 or 14 position, or secondary ester linkage is at the 5 or 6 position, or secondary ester linkage is at the 12 position, or secondary ester linkage is at the 14 position;
(3) unsaturated hydroxy derived estolide polyethylene glycol diesters:

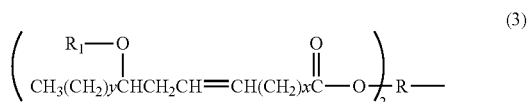

wherein x and y are each equal to 1 or greater than 1,
wherein x+y=from 8 to 18;
wherein R is a residual of a diol, wherein the diol may be any chain length of polyethylene glycol ($-CH_2-O-$);
wherein R is a residual of a triol;
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;
wherein the predominant species of secondary ester linkage is at the 9 or 10 position, or secondary ester linkage is at the 11 or 12 position, or secondary ester linkage is at the 13 or 14 position, or secondary ester linkage is at the 12 position, or secondary ester linkage is at the 14 position;
(4) estolide trimetholpropane (TMP) diesters:

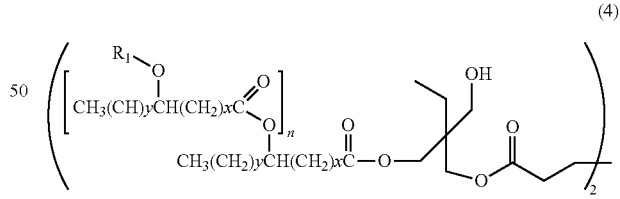

wherein x and y are each equal to 1 or greater than 1;
wherein x+y=from 11 to 21;
wherein n is 0, 1, or greater than 1;
wherein R1 is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;
wherein the predominant species of secondary ester linkage is at the 9 or 10 position, or secondary ester linkage is at the 11 or 12 position, or secondary ester linkage is at the 13 or 14 position, or secondary ester linkage is at the 5 or 6 position, or secondary ester linkage is at the 12 position, or secondary ester linkage is at the 14 position;

(5) hydroxy derived estolide trimetholpropane diesters:

$$\left( \begin{array}{c} R_1-O \\ | \\ CH_3(CH_2)_yCH(CH_2)_xC-O- \end{array} \begin{array}{c} O \\ \parallel \\ \end{array} \begin{array}{c} OH \\ \\ O \\ \\ O \end{array} \right)_2 \quad (5)$$

wherein x and y are each equal to 1 or greater than 1, wherein x+y=from 11 to 21;
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;
wherein the predominant species of secondary ester linkage is at the 9 or 10 position, or secondary ester linkage is at the 11 or 12 position, or secondary ester linkage is at the 13 or 14 position, or secondary ester linkage is at the 5 or 6 position, or secondary ester linkage is at the 12 position, or secondary ester linkage is at the 14 position;

(6) unsaturated hydroxy derived estolide trimetholpropane diesters:

$$\left( \begin{array}{c} R_1-O \\ | \\ CH_3(CH_2)_yCHCH_2CH=CH(CH_2)_xC-O- \end{array} \begin{array}{c} O \\ \parallel \\ \end{array} \begin{array}{c} OH \\ \\ O \\ \\ O \end{array} \right)_2 \quad (6)$$

wherein x and y are each equal to 1 or greater than 1, wherein x+y=from 8 to 18;
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;
wherein the predominant species of secondary ester linkage is at the 9 or 10 position, or secondary ester linkage is at the 11 or 12 position, or secondary ester linkage is at the 13 or 14 position, or secondary ester linkage is at the 12 position, or secondary ester linkage is at the 14 position;

(7) estolide epoxide polyethylene glycol diesters:

$$\left( \left[ \begin{array}{c} R_1 \\ \diagdown O \\ | \\ CH_3(CH_2)_wCH(CH_2)_zC \diagdown \\ O \end{array} \right]_n \begin{array}{c} O \\ \diagup \diagdown \\ H_3C(CH_2)_yCH-CH_2CH-CH-(CH_2)_xC-O \end{array} \begin{array}{c} O \\ \parallel \\ \end{array} \right)_2 R \quad (7)$$

wherein x and y are each equal to 1 or greater than 1, wherein x+y=from 8 to 18;
wherein x and y are each equal to 1 or greater than 1, wherein w+z=from 11 to 21;
wherein the predominant species of secondary ester linkage is at the 12 or 14 position,
wherein n is 0, 1, or greater than 1;
wherein R is a residual of a diol, wherein the diol may be any chain length of polyethylene glycol (—CH2-O—);
wherein R is a triol;
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;

(8) estolide dihydroxide polyethylene glycol diesters:

$$\left( \left[ \begin{array}{c} R_1 \\ \diagdown O \\ | \\ CH_3(CH_2)_wCH(CH_2)_zC \diagdown \\ O \end{array} \right]_n \begin{array}{c} OH \quad O \\ | \quad \parallel \\ H_3C(CH_2)_yCH-CH_2CH-CH-(CH_2)_xC-O \\ | \\ OH \end{array} \right)_2 R \quad (8)$$

wherein x and y are each equal to 1 or greater than 1, wherein x+y=from 8 to 18;
wherein x and y are each equal to 1 or greater than 1, wherein w+z=from 11 to 21;
wherein the predominant species of secondary ester linkage is at the 12 or 14 position,
wherein n is 0, 1, or greater than 1;
wherein R is a residual of a diol, wherein the diol may be any chain length of polyethylene glycol (—CH2-O—);
wherein R is a triol;
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;

(9) mono-capped hydroxy derived estolide epoxide polyethylene glycol diesters:

$$\left( \begin{array}{c} R_1 \\ \diagdown O \\ | \\ H_3C(CH_2)_yCH-CH_2CH-CH-(CH_2)_xC-O \end{array} \begin{array}{c} O \\ \diagup \diagdown \\ \end{array} \begin{array}{c} O \\ \parallel \\ \end{array} \right)_2 R \quad (9)$$

wherein x and y are each equal to 1 or greater than 1, wherein x+y=from 8 to 18
wherein the predominant species of secondary ester linkage is at the 12 or 14 position,
wherein R is a residual of a diol, wherein the diol is any chain length of polyethylene glycol (—CH2-O—);
wherein R is a triol;
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;

wherein the predominant species of secondary ester linkage is at the 9 or 10 position, or secondary ester linkage is at the 11 or 12 position, or secondary ester linkage is at the 13 or 14 position, or secondary ester linkage is at the 5 or 6 position or secondary ester linkage is at the 12 position, or secondary ester linkage is at the 14 position;

(10) mono-capped hydroxy derived estolide dihydroxide polyethylene glycol diesters:

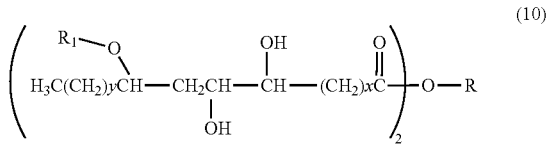

wherein x and y are each equal to 1 or greater than 1, wherein x+y=from 8 to 18;
wherein the predominant species of secondary ester linkage is at the 12 or 14 position,
wherein R is a residual of a diol, wherein the diol is any chain length of polyethylene glycol (—CH2-O—);
wherein R is a triol;
wherein $R_1$ is independently selected from hydrogen and a C1 to C36 fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;
and mixtures thereof; and optionally a carrier. All the compounds can be used as a viscosity index improver thereby improving a lubricant's performance. Also disclosed are methods to improve the viscosity index of a lubricant (e.g., mineral or polyalphaolefin (synthetic) base oils) involving of mixing (contacting) the above composition with a lubricant.

This summary is provided to introduce a selection of concepts in a simplified form that are further described below in the detailed description. This summary is not intended to identify key features or essential features of the claimed subject matter, nor is it intended as an aid in determining the scope of the claimed subject matter.

BRIEF DESCRIPTION OF THE DRAWINGS

Exemplary

DETAILED DESCRIPTION OF THE INVENTION

Figure 1:
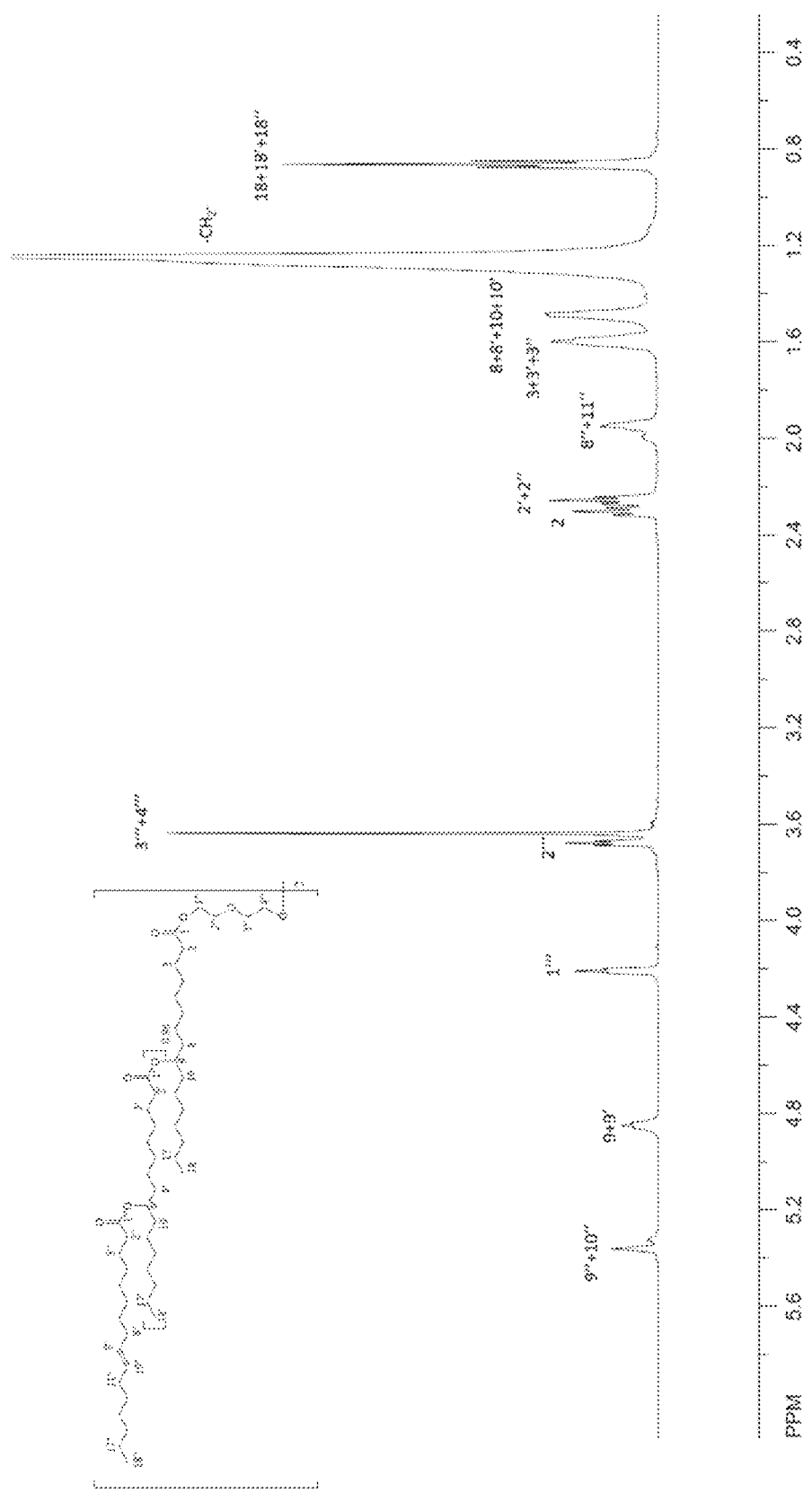
FIG. 1 shows $^1$H NMR of Oleic Estolide PEG-200 Diester (OE-PEG200-OE [7]) as described below.
Exemplary

Disclosed herein are compounds and compositions that can surprisingly be used as a viscosity index improver thereby improving lubricant performance. The compounds include the following (which may be used in combination with each other):

(1) estolide PEG diesters

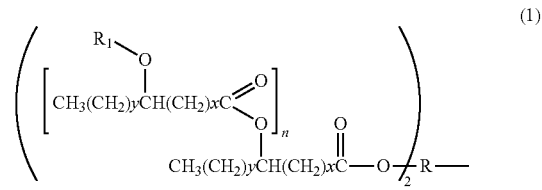

wherein x and y are each equal to 1 or greater than 1, wherein x+y=from 11 to 21;
wherein n is 0, 1, or greater than 1 (e.g., up to 9);
wherein R is a residual of a diol (residual means that it is derived from a diol since the R group is now a diester it would be inaccurate to name it as a diol, diol is just two alcohol groups, we are using primary alcohols since their reactivity is much greater than secondary or tertiary alcohols), wherein the diol may be any chain length of polyethylene glycol (—CH$_2$—O—) (e.g., there are a large variety of commercial polyethylene glycols with average molecular weights from about 100 to about 10,000, preferably PEG 200 and PEG 400), wherein examples of the diol include neopentyl glycol, propane diol, and hexanediol;
wherein R is a triol (e.g., triols that contain primary alcohols), wherein examples of the triol include trimetholpropane and glycerol;
wherein $R_1$ is independently selected from hydrogen and a $C_1$ to $C_{36}$ fatty acid (preferably $C_8$ to $C_{24}$) which may be saturated or unsaturated, branched or straight chain, and substituted or unsubstituted, or a residual fragment of oleic, ricinoleic, lesquerolic, stearic, lauric, capric, palmitic, myristic or other fatty acid chain;
wherein the predominant species (means here that there are a distribution of compounds but the main ones are centered around a particular position) of secondary ester linkage is at the 9 or 10 position (that is wherein x=7 or 8), or secondary ester linkage is at the 11 or 12 position (that is wherein x=9 or 10), or secondary ester linkage is at the 13 or 14 position (that is wherein x=11 or 12), or secondary ester linkage is at the 5 or 6 position (that is wherein x=3 or 4), or secondary ester linkage is at the 12 position (that is wherein x=10), or secondary ester linkage is at the 14 position (that is wherein x=12);

(2) hydroxy derived estolide PEG diesters:

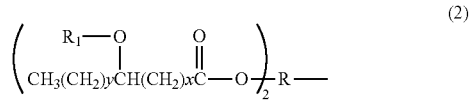

wherein x and y are each equal to 1 or greater than 1, wherein x+y=from 11 to 21;
wherein R is a residual of a diol, wherein the diol may be any chain length of polyethylene glycol (—CH$_2$—O—) (e.g., there are a large variety of commercial polyethylene glycols with average molecular weights from about 100 to about 10,000, preferably PEG 200 and PEG 400), wherein examples of the diol include neopentyl glycol, propane diol, and hexanediol;
wherein R is a triol (e.g., triols that contain primary alcohols), wherein examples of the triol include trimetholpropane and glycerol;

wherein $R_1$ is independently selected from hydrogen and a $C_1$ to $C_{36}$ fatty acid (preferably $C_8$ to $C_{24}$) which may be saturated or unsaturated, branched or straight chain, and substituted or unsubstituted, or a residual fragment of oleic, ricinoleic, lesquerolic, stearic, lauric, capric, palmitic, myristic or other fatty acid chain;

wherein the predominant species of secondary ester linkage is at the 9 or 10 position (that is wherein x=7 or 8), or secondary ester linkage is at the 11 or 12 position (that is wherein x=9 or 10), or secondary ester linkage is at the 13 or 14 position (that is wherein x=11 or 12), or secondary ester linkage is at the 5 or 6 position (that is wherein x=3 or 4), or secondary ester linkage is at the 12 position (that is wherein x=10), or secondary ester linkage is at the 14 position (that is wherein x=12);

(3) unsaturated hydroxy derived estolide polyethylene glycol diesters:

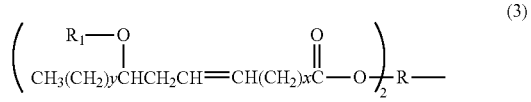

wherein x and y are each equal to 1 or greater than 1, wherein x+y=from 8 to 18;
wherein R is a residual of a diol, wherein the diol may be any chain length of polyethylene glycol (—$CH_2$—O—);
wherein R is a residual of a triol;
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, myristic or other fatty acid chain;
wherein the predominant species of secondary ester linkage is at the 9 or 10 position, or secondary ester linkage is at the 11 or 12 position, or secondary ester linkage is at the 13 or 14 position, or secondary ester linkage is at the 12 position, or secondary ester linkage is at the 14 position;

(4) estolide trimetholpropane (TMP) diesters:

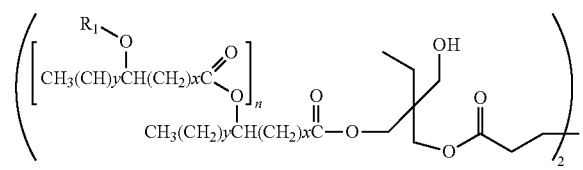

wherein x and y are each equal to 1 or greater than 1;
wherein x+y=from 11 to 21;
wherein n is 0, 1, or greater than 1 (e.g., up to 9);
wherein R1 is independently selected from hydrogen and a $C_1$ to $C_{36}$ fatty acid (preferably $C_8$ to $C_{24}$) which may be saturated or unsaturated, branched or straight chain, and substituted or unsubstituted, or a residual fragment of oleic, ricinoleic, lesquerolic, stearic, lauric, capric, palmitic, myristic or other fatty acid chain;
wherein the predominant species of secondary ester linkage is at the 9 or 10 position (that is wherein x=7 or 8), or secondary ester linkage is at the 11 or 12 position (that is wherein x=9 or 10), or secondary ester linkage is at the 13 or 14 position (that is wherein x=11 or 12), or secondary ester linkage is at the 5 or 6 position (that is wherein x=3 or 4), or secondary ester linkage is at the 12 position (that is wherein x=10), or secondary ester linkage is at the 14 position (that is wherein x=12);

(5) hydroxy derived estolide TMP diesters:

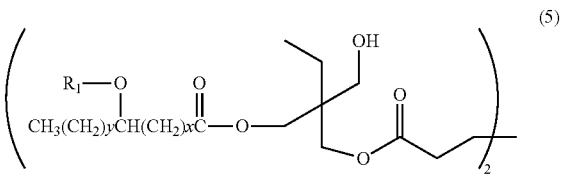

wherein x and y are each equal to 1 or greater than 1, wherein x+y=from 11 to 21;
wherein $R_1$ is independently selected from hydrogen and a $C_1$ to $C_{36}$ fatty acid (preferably $C_8$ to $C_{24}$) which may be saturated or unsaturated, branched or straight chain, and substituted or unsubstituted, or a residual fragment of oleic, ricinoleic, lesquerolic, stearic, lauric, capric, palmitic, myristic or other fatty acid chain;
wherein the predominant species of secondary ester linkage is at the 9 or 10 position (that is wherein x=7 or 8), or secondary ester linkage is at the 11 or 12 position (that is wherein x=9 or 10), or secondary ester linkage is at the 13 or 14 position (that is wherein x=11 or 12), or secondary ester linkage is at the 5 or 6 position (that is wherein x=3 or 4), or secondary ester linkage is at the 12 position (that is wherein x=10), or secondary ester linkage is at the 14 position (that is wherein x=12);

(6) unsaturated hydroxy derived estolide trimetholpropane diesters:

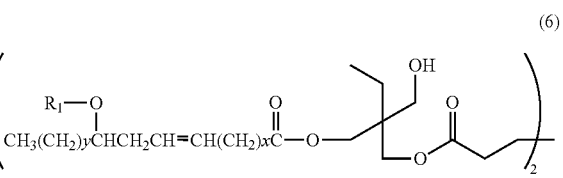

wherein x and y are each equal to 1 or greater than 1, wherein x+y=from 8 to 18;
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;
wherein the predominant species of secondary ester linkage is at the 9 or 10 position, or secondary ester linkage is at the 11 or 12 position, or secondary ester linkage is at the 13 or 14 position, or secondary ester linkage is at the 12 position, or secondary ester linkage is at the 14 position;

(7) estolide epoxide PEG diesters:

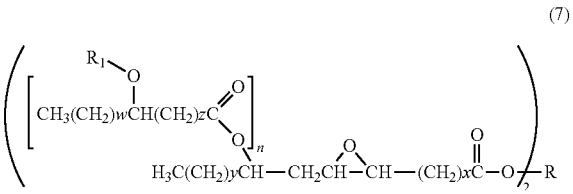

wherein the predominant species of secondary ester linkage is at the 12 or 14 position (that is wherein x=7 or 9 and y=5),
wherein n is 0, 1, or greater than 1 (e.g., up to 9);
wherein R is a residual of a diol, wherein the diol may be any chain length of polyethylene glycol (—CH2-O—) (e.g., there are a large variety of commercial polyethylene glycols with average molecular weights from about 100 to about 10,000, preferably PEG 200 and PEG 400), wherein examples of the diol include neopentyl glycol, propane diol, and hexanediol;
wherein R is a triol (e.g., triols that are all primary alcohols), wherein examples of the triol include trimetholpropane and glycerol;
wherein $R_1$ is independently selected from hydrogen and a $C_1$ to $C_{36}$ fatty acid (preferably $C_8$ to $C_{24}$) which may be saturated or unsaturated, branched or straight chain, and substituted or unsubstituted, or a residual fragment of oleic, ricinoleic, lesquerolic, stearic, lauric, capric, palmitic, myristic or other fatty acid chain;

(8) estolide dihydroxide PEG diesters:

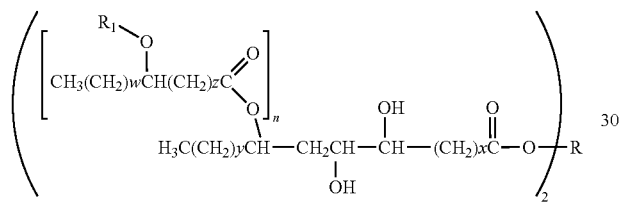

(8)

wherein the predominant species of secondary ester linkage is at the 12 or 14 position (that is wherein x=7 or 9 and y=5),
wherein n is 0, 1, or greater than 1 (e.g., up to 9);
wherein R is a residual of a diol, wherein the diol may be any chain length of polyethylene glycol (—CH2-O—) (e.g., there are a large variety of commercial polyethylene glycols with average molecular weights from about 100 to about 10,000, preferably PEG 200 and PEG 400), wherein examples of the diol include neopentyl glycol, propane diol, and hexanediol;
wherein R is a triol, wherein examples of the triol is trimetholpropane and glycerol;
wherein $R_1$ is independently selected from hydrogen and a $C_1$ to $C_{36}$ fatty acid (preferably $C_8$ to $C_{24}$) which may be saturated or unsaturated, branched or straight chain, and substituted or unsubstituted, or a residual fragment of oleic, ricinoleic, lesquerolic, stearic, lauric, capric, palmitic, myristic or other fatty acid chain;

(9) mono-capped hydroxy derived estolide epoxide PEG diesters:

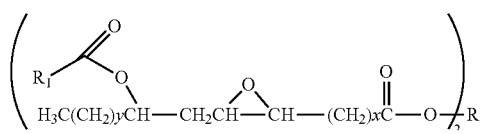

(9)

wherein the predominant species of secondary ester linkage is at the 12 or 14 position (that is wherein x=7 or 9 and y=5), wherein R is a residual of a diol, wherein the diol is any chain length of polyethylene glycol (—CH2-O—) (e.g., there are a large variety of commercial polyethylene glycols with average molecular weights from about 100 to about 10,000, preferably PEG 200 and PEG 400), wherein examples of the diol include neopentyl glycol, propane diol, and hexanediol;
wherein R is a triol (e.g., triols that are all primary alcohols), wherein examples of the triol include trimetholpropane and glycerol;
wherein $R_1$ is independently selected from hydrogen and a $C_1$ to $C_{36}$ fatty acid (preferably $C_8$ to $C_{24}$) which may be saturated or unsaturated, branched or straight chain, and substituted or unsubstituted, or a residual fragment of oleic, ricinoleic, lesquerolic, stearic, lauric, capric, palmitic, myristic or other fatty acid chain;
wherein the predominant species of secondary ester linkage is at the 9 or 10 position (that is wherein x=7 or 8), or secondary ester linkage is at the 11 or 12 position (that is wherein x=9 or 10), or secondary ester linkage is at the 13 or 14 position (that is wherein x=11 or 12), or secondary ester linkage is at the 5 or 6 position (that is wherein x=3 or 4) or secondary ester linkage is at the 12 position (that is wherein x=10), or secondary ester linkage is at the 14 position (that is wherein x=12); and

(10) mono-capped hydroxy derived estolide dihydroxide PEG diesters:

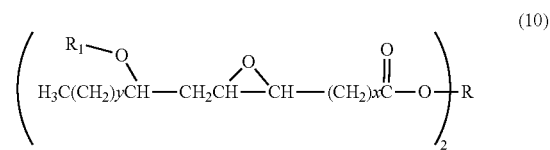

(10)

wherein the predominant species of secondary ester linkage is at the 12 or 14 position (that is wherein x=7 or 9 and y=5),
wherein R is a residual of a diol, wherein the diol is any chain length of polyethylene glycol (—CH2-O—) (e.g., there are a large variety of commercial polyethylene glycols with average molecular weights from about 100 to 10,000, preferably PEG 200 and PEG 400), wherein examples of the diol include neopentyl glycol, propane diol, and hexanediol;
wherein R is a triol (e.g., triols that are all primary alcohols), wherein examples of the triol include trimetholpropane and glycerol;
wherein $R_1$ is independently selected from hydrogen and a C1 to C36 fatty acid (preferably $C_8$ to $C_{24}$) which may be saturated or unsaturated, branched or straight chain, and substituted or unsubstituted, or a residual fragment of oleic, ricinoleic, lesquerolic, stearic, lauric, capric, palmitic, myristic or other fatty acid chain.

Also disclosed are methods to improve the viscosity index of a lubricant (e.g., mineral or polyalphaolefin (synthetic) base oils) involving of mixing (contacting) the above composition with a lubricant.

Other compounds known in the art (e.g., anti-oxidants, pour point depressants, cloud point depressants, anti-wear, extreme pressure, detergent) may be added to the composition provided they do not substantially interfere with the intended activity and efficacy of the composition; whether or not a compound interferes with activity and/or efficacy can be determined, for example, by the procedures utilized below.

"Optional" or "optionally" means that the subsequently described event or circumstance may or may not occur, and that the description includes instances in which said event or circumstance occurs and instances where it does not. For example, the phrase "optionally comprising a detergent" means that the composition may or may not contain a detergent and that this description includes compositions that contain and do not contain a detergent. Also, by example, the phrase "optionally adding a detergent" means that the method may or may not involve adding a detergent and that this description includes methods that involve and do not involve adding a detergent.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments and characteristics described herein and/or incorporated herein. In addition, the invention encompasses any possible combination that also specifically excludes any one or some of the various embodiments and characteristics described herein and/or incorporated herein.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions (e.g., reaction time, temperature), percentages and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 10% to a reference quantity, level, value, or amount. For example, about 1.0 g means 0.9 g to 1.1 g and all values within that range, whether specifically stated or not.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

The Examples refer to Schemes 1-6:

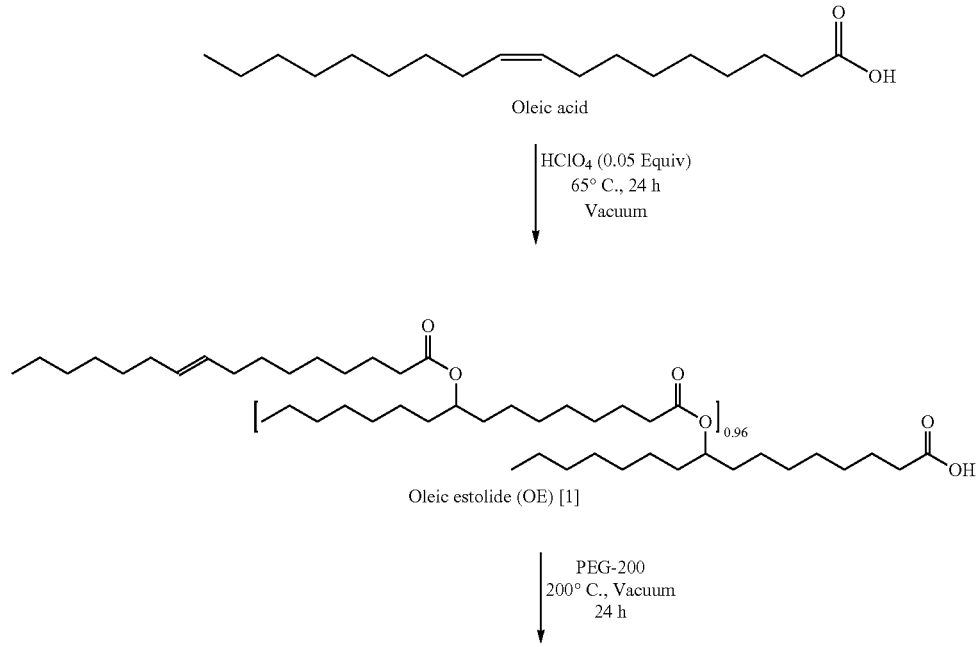

Scheme 1. Synthesis of Oleic Estolide PEG 200 Diester [7]

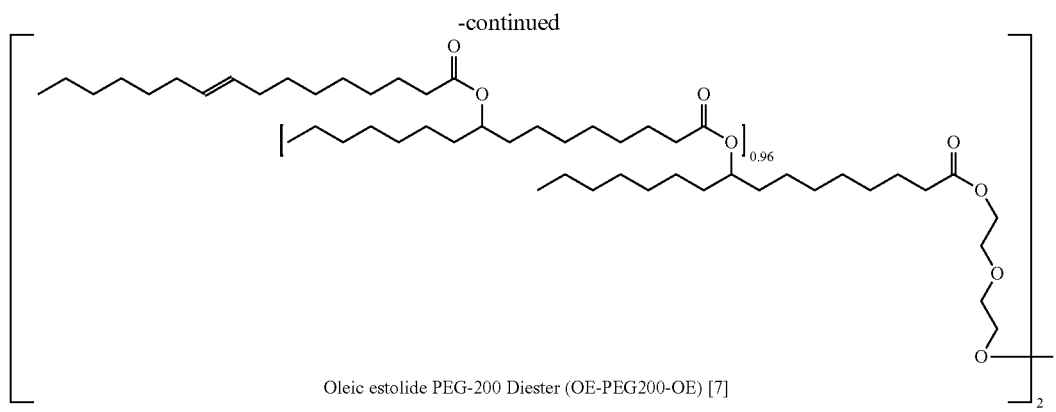
Oleic estolide PEG-200 Diester (OE-PEG200-OE) [7]
Scheme 2. Synthesis of 12-Hydroxystearate Homo-oligomer Polyestolide
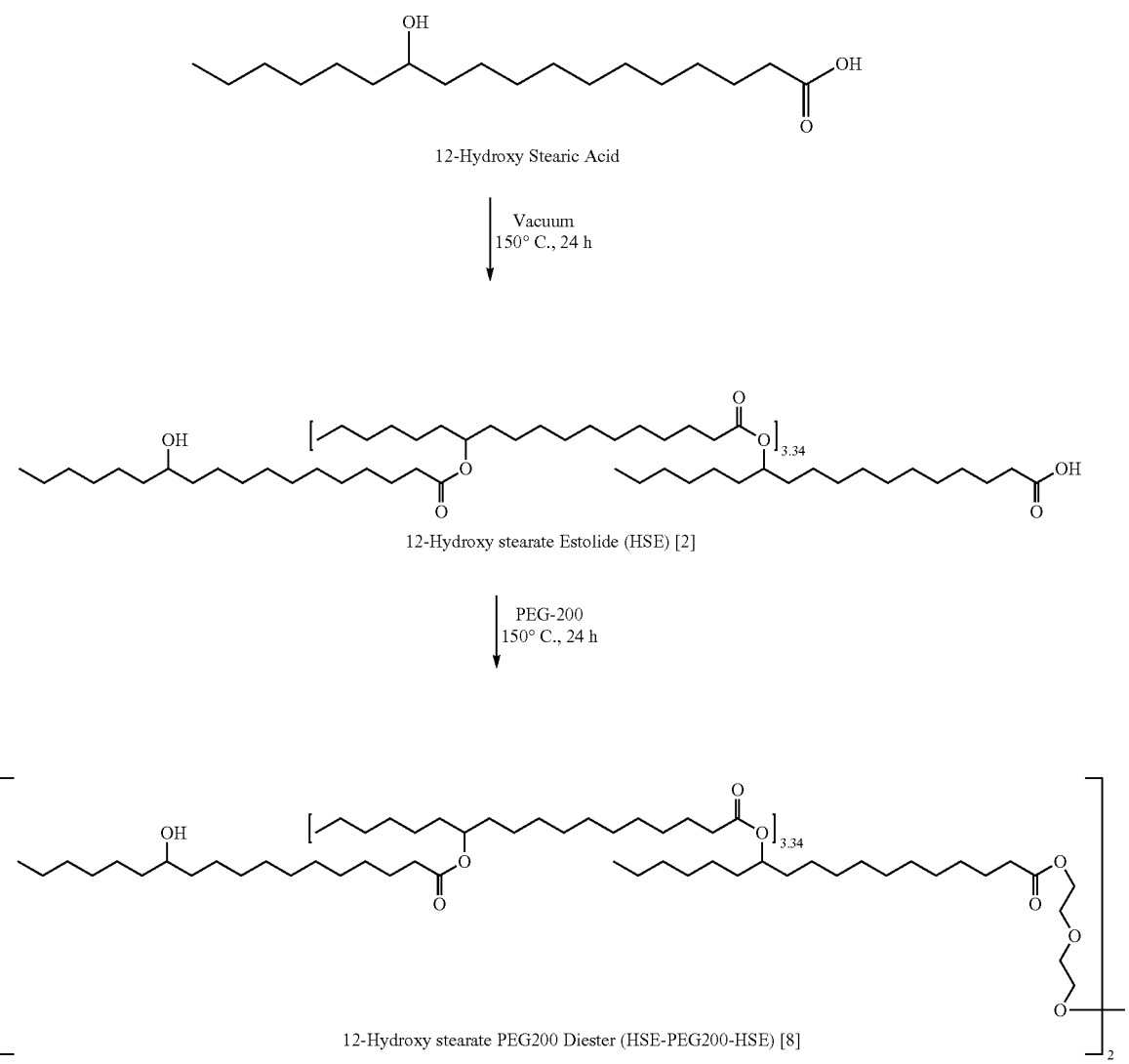

Scheme 3. Synthesis of Laurate Capped Ricinoleate Estolide PEG Diester Dihydroxy
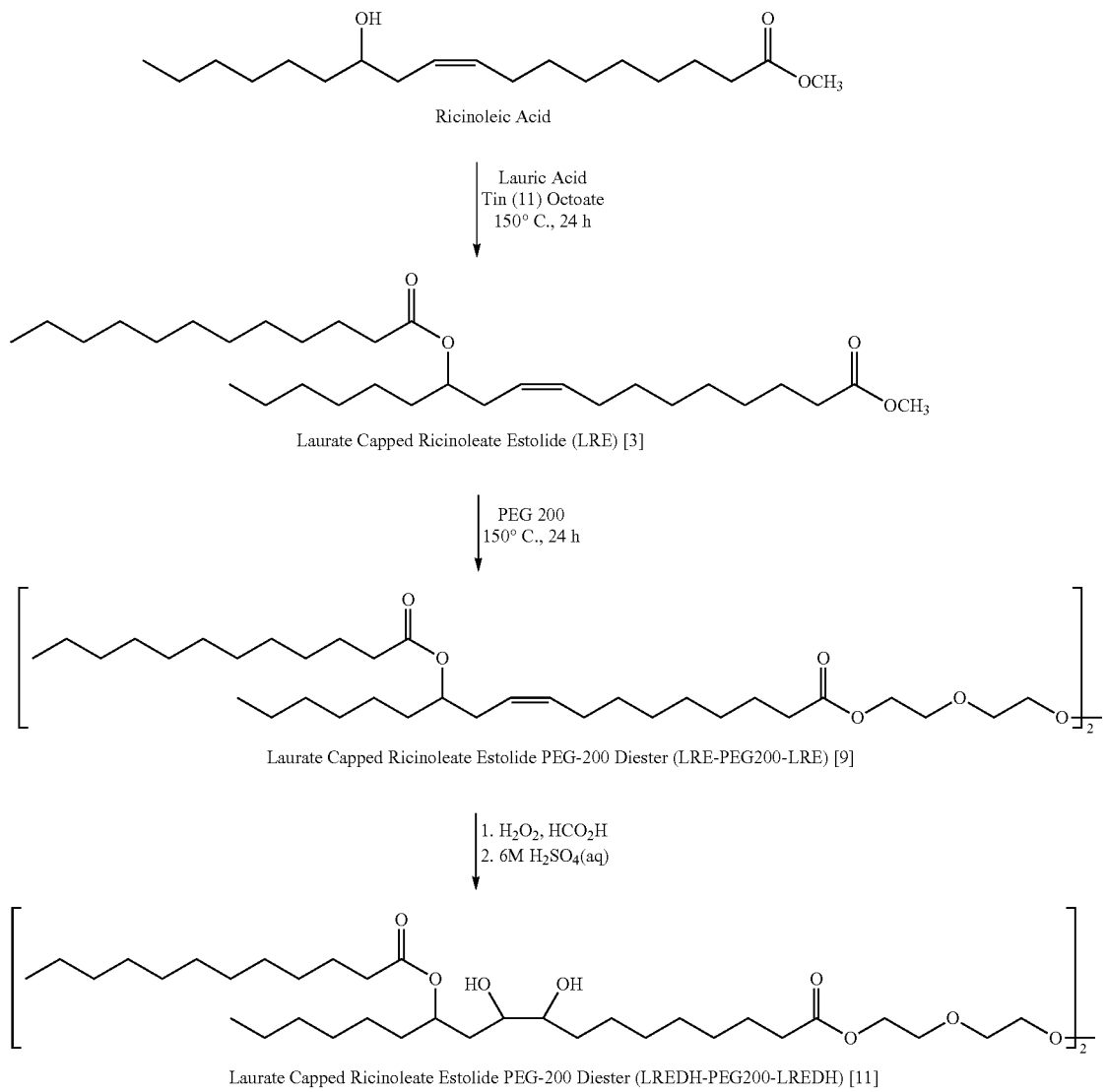
Scheme 4. Oleat Series
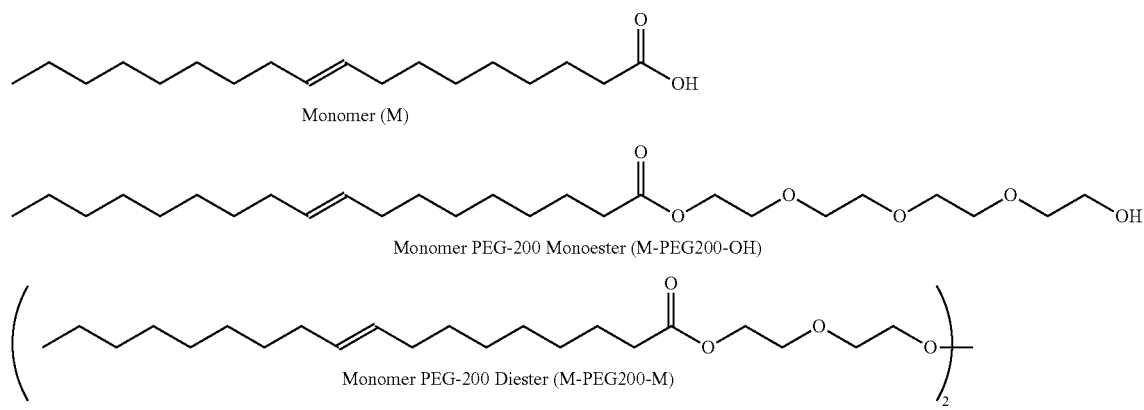

-continued

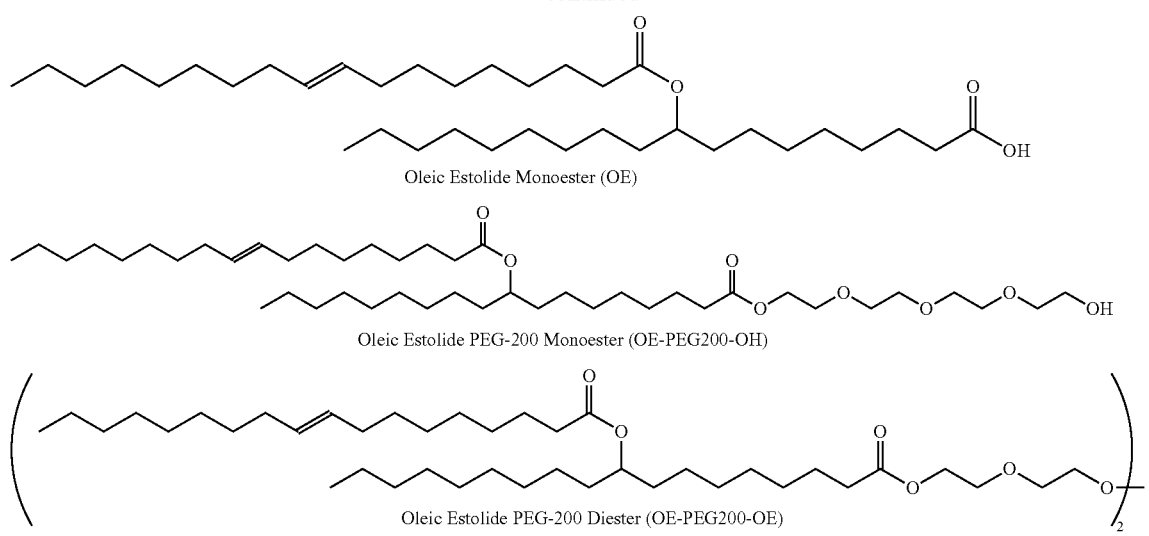

Oleic Estolide Monoester (OE)

Oleic Estolide PEG-200 Monoester (OE-PEG200-OH)

Oleic Estolide PEG-200 Diester (OE-PEG200-OE)

Scheme 5. Ricinoleate Series

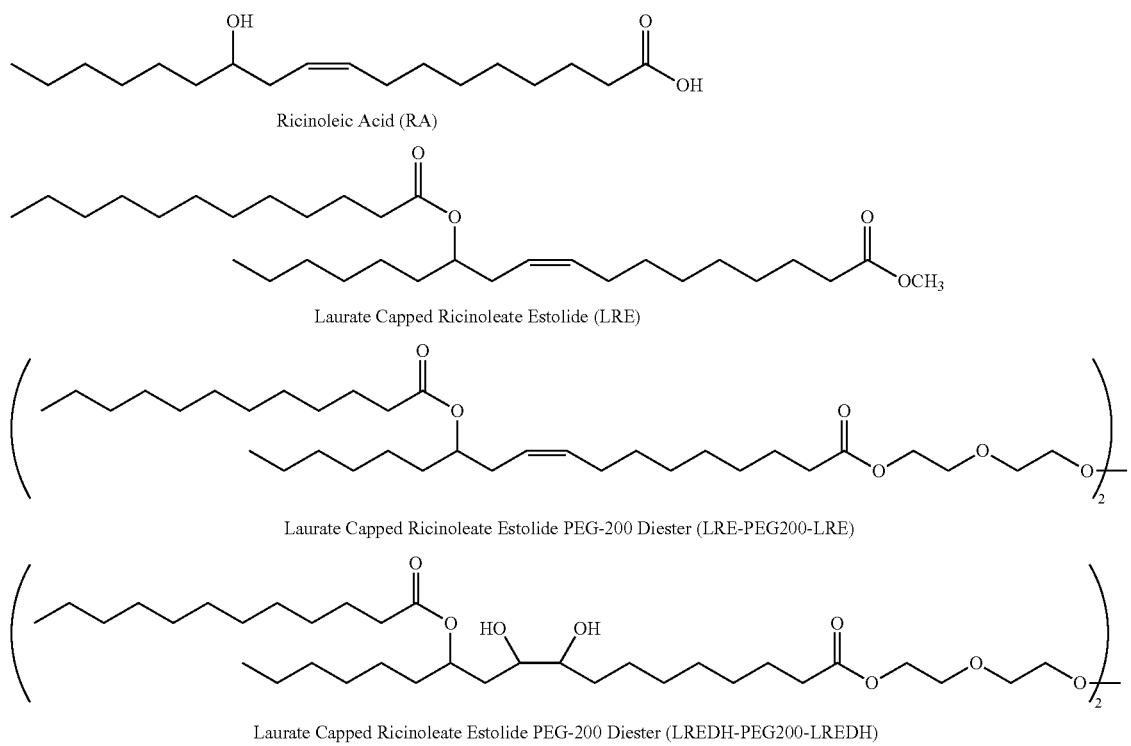

Ricinoleic Acid (RA)

Laurate Capped Ricinoleate Estolide (LRE)

Laurate Capped Ricinoleate Estolide PEG-200 Diester (LRE-PEG200-LRE)

Laurate Capped Ricinoleate Estolide PEG-200 Diester (LREDH-PEG200-LREDH)

Scheme 6. 12-Hydroxy Stearate Estolide Series

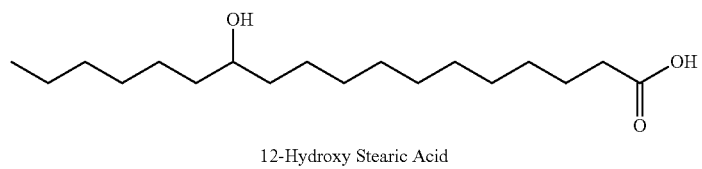

12-Hydroxy Stearic Acid

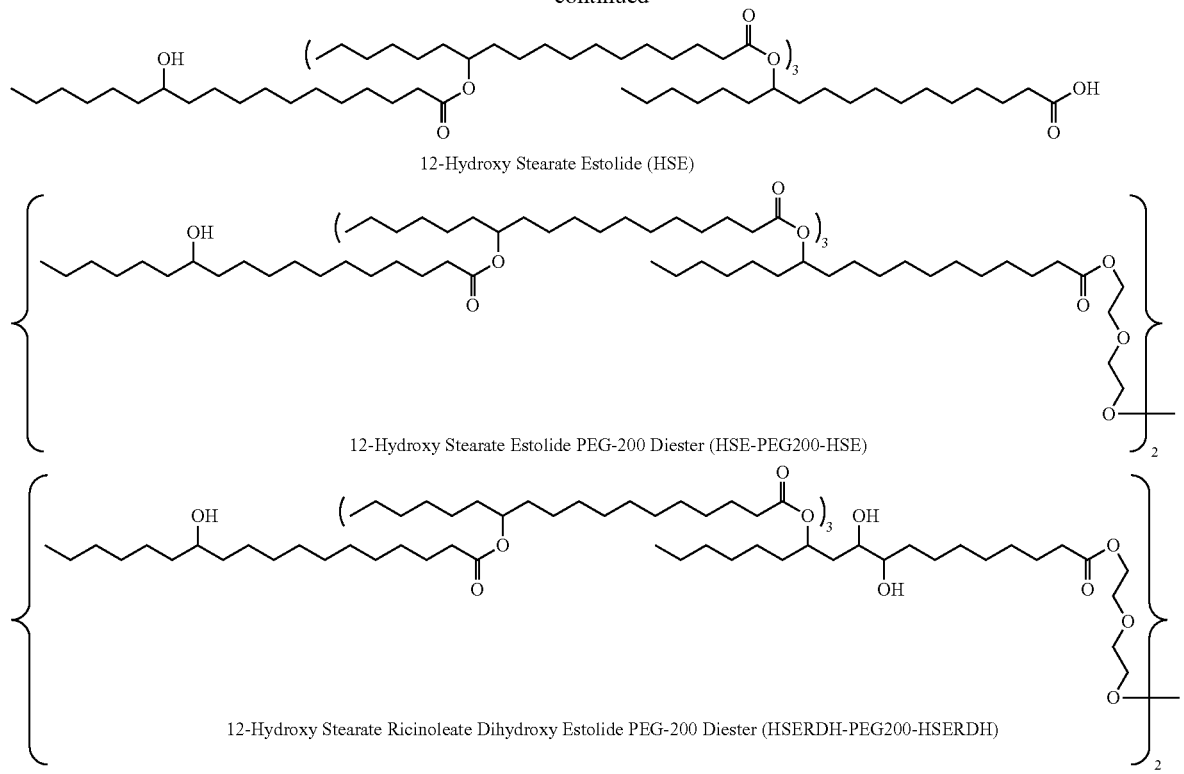

12-Hydroxy Stearate Estolide (HSE)

12-Hydroxy Stearate Estolide PEG-200 Diester (HSE-PEG200-HSE)

12-Hydroxy Stearate Ricinoleate Dihydroxy Estolide PEG-200 Diester (HSERDH-PEG200-HSERDH)

Materials: Oleic acid (90%), tin(II) 2-ethylhexanoate, polyethylene glycol-200 (PEG-200), polyethylene glycol-400 (PEG-400), and perchloric acid (70%) were purchased from Sigma-Aldrich Chemical Company, St. Louis, Mo. Dibasic phosphate, monobasic phosphate, castor oil, methanol, hexanes, ethyl acetate, tetrahydrofuran, and hydrogen peroxide (30%) were purchased from Fisher Chemical Company, Fair Lawn, N.J. Potassium hydroxide was purchased from EMD Millipore, Billerica, Mass. Formic acid (98%) and adipic acid were purchased from Acros Organics, Mullica Hill, N.J. 12-hydroxystearic acid was purchased from Alnor Oil Company, Valley Stream, N.Y. Sulfuric acid (98%) was purchased from LabChem Inc., Zelienople, Pa. Lauric acid was purchased from Pfaltz Bauer Inc., Waterbury, Conn. PAO 2 cST, PAO 4 cSt, PAO 8 cSt, 100N, 220N and 600 N base oils were a kind gift from Chevron Phillips (The Woodlands, Tex.). 1,6 Hexane diol was purchased from Spectrum Chemical (Gardena, Calif.) and distilled prior to use.

Instrumentation. Gas Chromatography (GC): Fatty acid analysis methods were used from Isbell & Kleiman (Isbell, T. A., and R. Kleiman, J. Am. Oil Chem. Soc., 71: 379-381 (1994)) as described below. Fatty acid analyses were conducted on an Agilent Technologies (Palo Alto, Calif.) 6890N GC equipped with a flame-ionization detector and an auto sampler/injector. GC separations were obtained on a SP-2380 30m×0.25 mm i.d. polysiloxane (90% biscyanopropyl/10% cyanopropylphenyl) capillary column from Supelco (Bellefonte, Pa.). Fatty acid methyl esters (FAMEs) were separated using a programmed temperature ramp from 150° C. to 265° C. at 10° C./min with a 5 min hold at 265° C. with a helium carrier gas flow rate of 1.4 mL/min at 138 kPa and a septum purge of 4.0 mL/min and a split ratio of 10:1. The injector and detector were maintained at 250° C. Saturated C8-C30 FAMEs provided standards for assigning peaks. A standard mix of C8-C30 saturated FAME GLC mixture supplied by Nu-Check Prep (Elysian, Minn.) which also contained FAMEs 18:1, 18:2, 18:3, 20:1, and 22:1 was used to identify retention times of fatty ester components in the estolide samples and calculate estolide number (EN) values for oleic estolide.

Nuclear Magnetic Resonance (NMR): $^1$H and $^{13}$C NMR experiments were recorded on a Bruker (Karlsruhe, Germany) Avance 500 spectrometer using a 5 mm broadband inverse (BBIO) probe with an absolute frequency of 500.11 MHz for $^1$H and 125.76 MHz for $^{13}$C. DEPT (distortionless enhancement by polarization transfer), COSY (correlated spectroscopy), HSQC (heteronuclear single quantum correlation), and HMBC (heteronuclear multiple bond correlation) two-dimensional spectra were also collected. Fifty milligrams of each sample were dissolved in 5 mL of 99.8% CDCl$_3$ (Cambridge Isotope Laboratories Inc., Andover, Mass.). Chemical shifts are expressed in ppm using the residual solvent peak as the internal standard. $^1$H experiments consisted of 16 scans, whereas 1024 scans were used in $^{13}$C experiments. Reported integration values for proton numbers can be multiplied by a factor to obtain whole numbers that correspond to an estolide number.

High Performance Liquid Chromatography (HPLC): HPLC separations of petroleum base oil from additive to determine the concentration of soluble additive in the base oil were conducted on Thermo Separations Spectra System P2000 gradient Pump coupled to an AS1000 autosampler/injector from Thermo Separations Products (Fremont, Calif.). Analytes were separated on a Luna 5 μm C8, 100 Å, 250×4.5 mm reverse phase column from Phenomenex (Torrance, Calif.). Compounds were eluted from the column using an isocratic flow of 100% acetone at 1 mL/min. A Varex ELSD III evaporative light scattering detector from Alltech Associates (Deerfield, Ill.) served as the detector where the dihydroxy derivatives had a retention time of 3.1 min and the base oil 4.5 min. A standard curve of LREDH-PEG200-LREDH (Scheme 5) with 7 data points spanning the concentration range 0.005 mg/mL to 3.062 mg/mL gave a linear response y=5.35×10$^{-5}$x+0.106 with an $R^2$=0.9995, F=3,750. A standard curve of HSERDH-PEG200-HSERDH (Scheme 6) with 6 data points spanning the concentration range 0.103 mg/mL to 4.136 mg/mL gave a linear response y=15549.5X-1269.8 with an $R^2$=0.9990, F=1,904. A standard curve of LREDH-HEXDIOL-LREDH with 4 data points spanning the concentration range 0.526 mg/mL to 3.091 mg/mL gave a linear response y=1359.9X-676.62 with an $R^2$=0.9949, F=391.

Methods. Methyl Ricinoleate: Castor oil (1,200 g, 1.29 moles) was placed in a 3 L three-neck round-bottom flask fitted with overhead stirrer, reflux condenser connected to tap water, and a glass stopper. The flask was located in a heating mantle controlled by a variac power supply. To the flask was added 324 mL of methanol and then the reaction mixture was warmed to methanol reflux with stirring. Sodium methoxide/methanol 30% solution (23.3 mL, 0.13 moles) was added to the flask at reflux with stirring. After 2 h, 84 mL of methanol was added and another 84 mL of methanol added 90 minutes later reflux continued with stirring. After another 90 min, a Dean-Stark trap was placed before the condenser and collected water of reaction (284 mL) over the next 90 min. The heating mantle was removed and the reaction was allowed to cool to room temperature at which point 0.5 M sulfuric acid/methanol (500 mL, 0.25 moles) was added and the reaction refluxed. After 2 h the reaction mixture was cooled to room temperature and transferred to a separatory funnel and the reaction was washed 2×100 mL of pH 5 buffer (0.5 M $NaH_2PO_4$) and the bottom aqueous layer was removed after each wash. The oil fraction was placed on a rotary evaporator at 50° C. and then on a Kügelrohr distillation apparatus at 110° C. under 7 Pa pressure to remove residual water and glycerin to yield 1,102 g of light yellow methyl ester (92% yield).

Oleic Estolide (OE) [1] (Scheme 1): Oleic acid (72% oleic, 92.7 kg, 329 moles) was placed in a 50 gallon Pfaudler glass lined reactor that had been acid washed and dried prior to charging. The reactor was fitted with a glass impeller, baffle, glass lined reflux condenser, and port connected to a mechanical vacuum pump to provide a reduced pressure in the vessel. To the stirred fatty acids, 70% perchloric acid ($HClO_4$) (1.40 L, 16.4 moles) was added and vigorous stirring was continued under vacuum (4.8 kPa) at 65° C. After 24 h, the reaction was quenched by adding potassium hydroxide (1.11 kg, 19.8 moles) in 4 L of 80% ethanol/$H_2O$ with vigorous stirring. The reaction was warmed to 85° C. with stirring under vacuum to remove ethanol/$H_2O$ which was collected with a modified Dean-Stark trap at the base of the condenser. The crude reaction mixture was filtered through a 5 μm bag filter to yield 86.7 kg of estolide (93.5% mass recovery). The reaction mixture contained 68.8% estolide with an EN of 1.96 and an acid value of 107.4 mg KOH/g of oil. Monomer (free fatty acids) was removed by Kügelrohr distillation (150°-185° C. at 7-11 Pa) to provide the purified estolide with an acid value 75.0 mg KOH/g oil. The purified estolide (OE) was used as the starting material for all subsequent reactions that used the oleic estolide. $^1$H NMR ($CDCl_3$): δ 5.38 (m, 1H, —HC=CH—), 4.87 (m, 1H, R—, $R_1$—CH—$O_2$C—$R_2$), 2.34 (t, J=7.48 Hz, 1.3H, —$CH_2$—$CO_2$H), 2.28 (m, 2.2H, —$CH_2CO_2$—CH—R, —$R_1$), 2.07-1.90 (m, 2H, —$CH_2$—C=C—$CH_2$—), 1.63 (m, 3.6H, —$CH_2$—$CH_2$—$CO_2$—), 1.51 (m, 4.4H, —$CH_2$—CH—($O_2$C—R)—$CH_2$—), 1.24 (m, 36.4H, —$CH_2$—), and 0.88 (m, 5.2H, —$CH_3$) ppm. $^{13}$C NMR ($CDCl_3$): □□179.8-179.7 (6 signals, R—$CO_2$—CH—$R_1$, —$R_2$), 173.7 and 173.7 (R—$CO_2$—$CH_3$), 130.5-129.9 (9 signals, —HC=CH—), 74.1-74.0 (3 signals, $R_1$—, $R_2$—HC—$O_2$C—$R_3$), 34.7 (—$CH_2$—$CO_2$—CH—$R_1$, —$R_2$), 34.1 (3 signals, —$CH_2$—$CO_2$—$CH_3$), 32.6-31.7 (9 signals, —$CH_2$—CH—(—$O_2$C—R)—$CH_2$—), 29.9-28.8 (multiple signals, —$CH_2$—), 25.3-24.6 (multiple signals, —$CH_2$—$CH_2$—$CO_2$—R), 22.7-21.3 (multiple signals, R—$CH_2$—$CH_3$) and 14.1-14.0 (3 signals, —$CH_2$—$CH_3$) ppm.

12-Hydroxystearate estolide (HSE) [2] (Scheme 2): 12-Hydroxystearic acid (70.5 g, 234.9 mmoles) which already contained homopolymeric estolides was further polymerized by placing the mixture into a 250 mL round-bottom flask under vacuum (~2 kPa) at 150° C. for 24 h. This gave the HSE estolide in quantitative yield with an EN of 4.34 and an acid value of 58.6 mg KOH/g oil. $^1$H NMR ($CDCl_3$): δ 4.85 (m, 4.3H, R—, $R_1$—CH—$O_2$C—$R_2$), 3.58 (m, 1.0H, R—, $R_1$—CH—OH), 2.32 (, J=7.44 Hz, 3.7H, —$CH_2$—$CO_2$H), 2.26 (t, J=7.41 Hz, 8.7H, —$CH_2CO_2$—CH—R, —$R_1$), 1.60 (m, 12.7H, —$CH_2$—$CH_2$—$CO_2$—), 1.49 (m, 18.3H, —$CH_2$—CH—($O_2$C—R)—$CH_2$—), 1.42 (m, 6.6H, —$CH_2$—CH—(OH)—$CH_2$—), 1.25 (m, 139.2H, —$CH_2$—) and 0.88 (m, 16.8H, —$CH_3$) ppm. $^{13}$C NMR ($CDCl_3$): δ 179.3-179.1 (4 signals, R—$CO_2$H), 173.7 (R—$CO_2$—CH—$R_1$, —$R_2$), 74.1 ($R_1$—, $R_2$—HC—$O_2$C—$R_3$), 72.1 (R—, $R_1$—CH—OH), 37.4 (2 signals —$CH_2$—CH—(OH)—$CH_2$—), 34.7 (—$CH_2$—$CO_2$H), 34.2 (—$CH_2$—$CO_2$—CH—$R_1$, $R_2$), 34.0 (—$CH_2$—), 31.9-31.8 (t, 3 signals, —$CH_2$—CH—($O_2$C—R)—$CH_2$—), 29.7-29.0 (multiple signals, —$CH_2$—), 25.6-24.7 (multiple signals, —$CH_2$—$CH_2$—$CO_2$—R), 22.7-22.6 (3 signals, R—$CH_2$—$CH_3$) and 14.1-14.0 (multiple signals, —$CH_2$—$CH_3$) ppm.

Laurate capped methyl ricinoleate estolide (LRE) [3] (Scheme 3): (50.0 g, 0.16 moles) and lauric acid (128.2 g, 0.64 moles) were placed in a 500 mL round-bottom flask equipped with a magnetic stir bar and vacuum adapter. Tin(I) octoate (0.5 mL, 0.002 moles) was added to the mixture and the flask warmed to 150° C. in a heating mantle controlled by a temperature controller. The reaction was stirred under vacuum at 150° C. for 24 h at which point the excess lauric acid was removed by Kügelrohr distillation (17° C. at 7 Pa) to yield a residue of 62.5 g (0.126 moles), 79.0% isolated mass yield of LRE product, and 106.1 g of lauric acid distillate. $^1$H NMR ($CDCl_3$): δ 5.45 (m, 1H, —CH—(OH)—$CH_2$—HC=CH—) δ 5.34 (m, 1H, —CH—(OH)—$CH_2$—HC=CH—), 4.88 (m, 1H, R—, $R_1$—CH—$O_2$C—$R_2$), 3.66 (s, 2.6H, R—$CO_2$—$CH_3$), 2.32-2.25 (m, 6.2H, —$CH_2$—$CO_2CH_3$ and —$CH_2$—$CO_2$—CH—R—, —R and —CH(—$O_2$C—$R_3$)—$CH_2$—CH=CH—), 2.03-2.00 (m, 2.1H, —$CH_2$—CH(—$O_2$C—R)—CH=CH—$CH_2$—), 1.63-1.59 (m, 4.2H, —$CH_2$—$CH_2$—$CO_2$—), 1.55- 1.52 (m, 2.1H, —$CH_2$—CH(—$O_2$C—R)—$CH_2$—), 1.27 (m, 33.8H, —$CH_2$—) and 0.88 (m, 6.2H, —$CH_3$) ppm. $^{13}$C NMR ($CDCl_3$): δ 174.2 (R—$CO_2CH_3$), 173.5 (R—$CO_2$—CH—$R_1$—, —$R_2$), 132.5 (R—CH—(OH)—$CH_2$—HC=CH—), 124.3 (—CH(—$O_2$C—R)—$CH_2$—HC=CH—), 73.6 ($R_1$—, $R_2$—HC—$O_2$C—$R_3$), 71.5 (R—CH—(OH)—$R_1$), 51.4 (—$CO_2$—$CH_3$) 34.7 (—$CH_2$—$CO_2CH_3$), 34.1 (—$CH_2$—$CO_2$—CH—R, $R_1$), 33.6 (R—, $R_1$—$CO_2$—CH—$CH_2$—CH=CH—), 29.6-29.0 (multiple signals, —$CH_2$—), 27.3 (—CH=CH—$CH_2$—), 25.3-24.8 (3 signals, —$CH_2$—$CH_2$—$CO_2$—R), 22.7-22.6 (3 signals, R—$CH_2$—$CH_3$) and 14.1-14.0 (3 signals, —$CH_2$—$CH_3$) ppm.

Monomer polyethylene glycol-200 monoester (M-PEG200-OH) [4] (Scheme 4): PEG-200 monoester was synthesized by placing monomer (i.e., the distillate from the estolide reaction) (25.0 g, 88.6 mmoles) that had been distilled from the synthesis of oleic estolide in a 100 mL three-neck round-bottom flask fitted with a condenser capped with a vacuum port, glass stopper, temperature probe, and magnetic stir bar. PEG-200 (62.9 mL, 354.6 mmoles) was added to the flask which was warmed to 200° C. under vacuum (~2 kPa). After 24 h the mixture was placed in a distilling flask and Kügelrohr distilled (168° C. at 9 Pa) to yield 38.4 g of monomer PEG-200 monoester with an acid value of 1.1 mg KOH/g oil. $^1$H NMR (CDCl$_3$): δ 5.34 (m, 1.5H, —HC=CH—), 4.17 (m, 2.4H, —CO$_2$—CH$_2$CH$_2$—O—), 3.68 (m, 2.2H, —O—CH$_2$CH$_2$—OH), 3.65 (m, 1.95H—CO$_2$—CH$_2$CH$_2$—O—), 3.62 (m, 11.8H, R—O—CH$_2$CH$_2$—O—R), 3.57 (m, 2.2H—O—CH$_2$CH$_2$—OH), 3.09 (s, 1.6H, —OH), 2.28 (m, 2.0H, —CH2CO$_2$—R), 1.93 (m, 3.1H, —CH$_2$—CH=CH—CH$_2$—), 1.58 (m, 2.1H, —CH$_2$—CH$_2$—CO$_2$—R), 1.22 (m, 20.4H, —CH$_2$—) and 0.84 (m, 3.0H, —CH$_3$) ppm. $^{13}$C NMR (CDCl$_3$): δ 173.8 (R—CO$_2$—R$_1$), 130.6-129.9 (multiple signals, —HC=CH—), 72.5 (multiple signals, —O—CH$_2$CH$_2$—OH), 70.6-70.2 (multiple signals, R—O—CH$_2$CH$_2$—O—R$_1$), 69.2 (R—CO$_2$—CH$_2$CH$_2$—O—), 63.3 (3 signals, R—CO$_2$—CH$_2$CH$_2$—O—), 61.6 (3 signals, —O—CH$_2$CH$_2$—OH), 34.1 (—CH$_2$—CO$_2$—R), 32.5 (9 signals, —CH$_2$—CH=CH—CH$_2$—), 31.9-28.6 (multiple signals, —CH$_2$—), 24.9 (—CH$_2$—CH$_2$—CO$_2$—R), 22.6 (R—CH$_2$—CH$_3$) and 14.1 (—CH$_2$—CH$_3$) ppm.

Oleic estolide polyethylene glycol-200 mono-ester (OE-PEG200-OH) [5] (Scheme 4): PEG-200 monoester was synthesized by placing oleic estolide (25.0 g, 33.4 mmoles) in a 100 mL three-neck round-bottom flask fitted with a condenser capped with a vacuum port, glass stopper, temperature probe, and magnetic stir bar. PEG-200 (23.8 mL, 133.6 mmoles) was added to the flask which was warmed to 200° C. under vacuum (~2 kPa). After 24 h the contents were placed in a distilling flask and Kügelrohr distilled (124°-180° C. at 9 Pa) to yield 31.6 g of oleic estolide PEG-200 monoester with an acid value of 1.7 mg KOH/g oil. $^1$H NMR (CDCl$_3$): δ 5.35 (m, 2.4H, —HC=CH—), 4.84 (m, 1.5H, R—, R$_1$—CH—O$_2$C—R$_2$), 4.19 (m, 2.0H, —CO$_2$—CH$_2$CH$_2$—O—), 3.70 (m, 2.2H, —O—CH$_2$CH$_2$—OH), 3.65 (m, 2.3H, —CO$_2$—CH$_2$CH$_2$—O—), 3.64 (m, 10.3H, —O—CH$_2$CH$_2$—O—), 3.59 (m, 2.0H, —O—CH$_2$CH$_2$—OH), 2.91 (s, 1.3H, —OH), 2.29 (m, 2.0H, —CH$_2$CO$_2$—R), 2.25 (t, J=7.41 Hz, 2.5H, —CH$_2$CO$_2$—CH—R, R$_1$), 1.94 (m, 2.7H, —CH$_2$—CH=CH—CH$_2$—), 1.59 (m, 4.6H, —CH$_2$—CH$_2$—CO$_2$—R), 1.48 (m, 4.9H, —CH$_2$—CH(—O$_2$C—R)—CH$_2$—), 1.24 (m, 47.9H, —CH$_2$—) and 0.86 (m, 7.3H, —CH$_3$) ppm. $^{13}$C NMR (CDCl$_3$): δ173.2 (R—CO$_2$—R$_1$), 130.1 (multiple signals, —HC=CH—), 73.9 (R$_1$—, R$_2$—HC—O$_2$C—R$_3$), 72.5 (2 signals, —O—CH$_2$CH$_2$—OH), 70.6-70.2 (multiple signals, —O—CH$_2$CH$_2$—O—), 69.1 (multiple signals, R—CO$_2$—CH$_2$CH$_2$—O—), 63.2 (3 signals, R—CO$_2$—CH$_2$CH$_2$—O—), 61.6 (3 signals, —O—CH$_2$CH$_2$—OH), 34.6 (R—, R$_1$—CH(—O$_2$C—CH$_2$—R$_2$), 34.1 (—CH$_2$—CO$_2$—R), 32.5 and 31.8 (multiple signals, —(H$_2$—CH=CH—CH$_2$—), 29.7-28.6 (multiple signals, —CH$_2$—), 25.3 (multiple signals, —CH$_2$—CH$_2$—CO$_2$—R), 22.6 (multiple signals, R—CH$_2$—CH$_3$) and 14.1 (—CH$_2$—CH$_3$) ppm.

Monomer polyethylene glycol-200 diesters (M-PEG200-M) [6] (Scheme 4): PEG-200 diesters were synthesized by placing monomer (i.e., the distillate from the estolide reaction) (25.0 g, 88.7 mmoles) that had been distilled from the synthesis of oleic estolide in a 100 mL three-neck round-bottom flask fitted with a condenser capped with a vacuum port, glass stopper, temperature probe, and magnetic stir bar. PEG-200 (7.90 mL, 44.3 mmoles) was added to the flask which was warmed to 200° C. under vacuum (~2 kPa). After 24 h the contents were removed from heat to obtain monomer PEG-200 diester with an acid value of 6.7 mg KOH/g oil. $^1$H NMR (CDCl$_3$): δ 5.34 (m, 1.4H, —HC=CH—), 4.19 (m, 1.7H, —CO$_2$—CH2CH$_2$—O—), 3.65 (m, 1.8H, —C$_2$—CH$_2$CH$_2$—O—), 3.61 (m, 4.2H, R—O—CH$_2$CH$_2$—O—R), 2.28 (m, 2.0H, —CH$_2$CO$_2$—R), 1.93 (m, 3.0H, —CH$_2$—CH=CH—CH$_2$—), 1.58 (m, 2.1, —CH$_2$—CH$_2$—CO$_2$—R), 1.22 (m, 19.9H, —CH$_2$—) and 0.84 (m, 3.0H, —CH$_3$) ppm. $^{13}$C NMR (CDCl$_3$): δ 173.8 (R—CO$_2$—R$_1$), 130.6-129.9 (multiple signals, —HC=CH—), 70.6-70.5 (multiple signals, R—O—CH$_2$CH$_2$—O—R), 69.2 and 69.2 (R—CO$_2$—CH$_2$CH$_2$—O—), 63.3 (3 signals, R—CO$_2$—CH$_2$CH$_2$—O—), 34.2 (—CH$_2$—CO$_2$—R), 32.5 (multiple signals, —CH$_2$—CH=CH—CH$_2$—), 29.7-28.7 (multiple signals, —CH$_2$—), 24.9 (—CH$_2$—CH$_2$—CO$_2$—R), 22.7 (R—CH$_2$—CH$_3$) and 14.1 (—CH$_2$—CH$_3$) ppm.

Oleic estolide polyethylene glycol-200 (OE-PEG200-OE) diesters [7] (Scheme 4): PEG-200 diesters were synthesized by placing oleic estolide (25 g, 34.7 mmoles) in a 100 mL three-neck round-bottom flask fitted with a condenser capped with a vacuum port, glass stopper, temperature probe, and magnetic stir bar. PEG-200 (3.1 mL, 17.3 mmoles) were added to the flask which was warmed to 200° C. under vacuum (~2 kPa). After 24 h the contents were removed from heat to obtain oleic estolide PEG-200 diester with an EN of 1.96 and an acid value of 3.2 mg KOH/g oil. $^1$H NMR (CDCl$_3$): δ 5.36 (m, 1.4H, —HC=CH—), 4.85 (m, 1H, R—, R$_1$—CH—O$_2$C—R$_2$), 4.20 (m, 2.0H, —CO$_2$—CH$_2$CH$_2$—O—), 3.67 (m, 2.1H, —CO$_2$—CH$_2$CH$_2$—O—), 3.64 (m, 4.9H, —O—CH$_2$CH$_2$—O—), 2.30 (m, 2.2H, —CH$_2$—CO$_2$—R), 2.28 (m, 3.2H, —CH$_2$—CO$_2$—CH—R, —R$_1$), 1.95 (m, 3.1H, —CH$_2$—CH=CH—CH$_2$—), 1.60 (m, 57H, —CH$_2$—CH$_2$—CO$_2$—R), 1.49 (m, 6.6H, —CH$_2$—CH—(O$_2$C—R)—CH$_2$—), 1.24 (m, 54.6H, —CH$_2$—) and 0.86 (m, 8.0H, —CH$_3$) ppm. $^{13}$C NMR (CDCl$_3$): δ 173.6 (multiple signals, R—CO$_2$—R$_1$), 130.0 (multiple signals, —HC=CH—), 73.9-73.8 (R$_1$—, R$_2$—HC—O$_2$C—R$_3$), 70.5-70.5 (multiple signals, —O—CH$_2$CH$_2$—O—), 69.2 and 69.1 (R—CO$_2$—CH$_2$CH$_2$—O—), 63.2 and 63.2 (R—CO$_2$—(CH$_2$CH$_2$—O—), 34.6 (—CH$_2$—CO$_2$—R), 34.1 (—CH$_2$—CO$_2$—CH—R$_1$, —R$_2$), 32.5-31.7 (multiple signals, —CH$_2$—CH=CH—CH$_2$—), 29.6-28.7 (multiple signals, —CH$_2$—), 25.2-24.7 (multiple signals, —CH$_2$—CH$_2$—CO$_2$—R), 22.6-22.4 (multiple signals, R—CH$_2$—CH$_3$) and 14.0-13.9 (3 signals, —CH$_2$—CH$_3$) ppm.

12-Hydroxystearate estolide polyethylene glycol-200 diesters (HSE-PEG200-HSE) [8] (Scheme 6): PEG-200 diesters were synthesized by placing 12-hydroxystearate estolide (HSE) (25 g, 18 mmoles) in a 100 mL three-neck round-bottom flask fitted with a condenser capped with a vacuum port, glass stopper, temperature probe, and magnetic stir bar. PEG-200 (1.6 mL, 9.0 mmoles) were added to the flask which was warmed to 150° C. under vacuum (~2 kPa). After 24 h the contents were cooled to room temperature to yield 12-hydroxystearate estolide PEG-200 diester (HSE-PEG200-HSE) with an EN of 4.34 and an acid value of 10.08 mg KOH/g oil. $^1$H NMR (CDCl$_3$): δ 4.86 (m, 3.2H, R—, R$_1$—CH—O$_2$C—R$_2$), 4.21 (m, 1.3H, —C$_2$—CH$_2$CH$_2$—O—), 3.69 (m, 1.4H, —CO$_2$—CH$_2$CH$_2$—O—), 3.64 (m, 3.3H, —O—CH$_2$CH$_2$—O—), 3.59 (m, 0.4H, R—, R$_1$—CH—OH), 2.31 (m, 2.0H, —CH$_2$CO$_2$—R), 2.27 (t, J=7.4 Hz, 3.2H, —CH$_2$—CO$_2$—CH—R, —R$_1$), 1.61 (m, 8.7H, —CH$_2$—CH$_2$—CO$_2$—R), 1.50 (m, 13.6H, —CH$_2$—CH—(O$_2$C—R)—CH$_2$—), 1.25 (m, 98.0H, —CH2-) and 0.87 (m, 13.1H, —CH3) ppm. $^{13}$C NMR (CDCl$_3$): δ 173.8 (R—CO$_2$—R$_1$), 173.7 (R—C$_2$-C$_H$—R$_1$, —R$_2$), 74.0 (R$_1$—, R$_2$—HC—O$_2$C—R$_3$), 72.0 (—CH—OH), 70.6-70.6 (multiple signals, —O—CH$_2$CH$_2$—O—), 69.2 (R—C$_2$—CH$_2$CH$_2$—O—), 63.1 (R—C$_2$—CH$_2$CH$_2$—O—), 37.5 (—CH$_2$—CH(OH)—CH$_2$—), 34.7 (—CH$_2$—CO$_2$—CH—R$_1$, —R$_2$), 34.1 (—(H$_2$—CO$_2$—R), 34.2 (—CH$_2$—CH—(O$_2$C—R)—CH$_2$—), 31.9-29.6 (multiple signals, —CH$_2$—), 25.3-24.9 (multiple signals, —CH$_2$—CH$_2$—CO$_2$—R), 22.7-22.6 (multiple signals, R—CH$_2$—CH$_3$), 14.1 and 14.0 (—CH$_2$—CH$_3$) ppm.

Laurate capped ricinoleate estolide polyethylene glycol-200 diester (LRE-PEG200-LRE) [9] (Scheme 3): Laurate capped methyl ricinoleate estolide (LRE) (62.5 g, 0.126 moles) was placed in a 500 mL round-bottom flask equipped with a magnetic stir bar and vacuum adapter. Tin(II) octoate (0.7 mL, 0.002 moles) and PEG-200 (7.5 mL, 42.1 mmoles) were added to the mixture and the flask warmed to 150° C. in a heating mantle controlled by a temperature controller. The reaction was stirred under vacuum at 150° C. at ~2 kPa for 24 h at which point the excess estolide was removed by Kügelrohr distillation (225° C. at 9 Pa) to yield a residue of 56.11 g (0.126 moles) 79.0% isolated mass yield of brown oil diester product (LRE-PEG200-LRE). $^1$H NMR (CDCl$_3$): δ 5.43 (m, 1.0H, —CH(O$_2$C—R)—CH$_2$—HC═CH—), 5.30 (m, 1.0H, —CH(O$_2$C—R)—CH$_2$—HC═CH—), 4.86 (m, 1.0H, R—, R$_1$—CH—(O$_2$C—R$_2$)), 4.20 (m, 1.4H, —CO$_2$—CH$_2$CH$_2$—O—), 3.67 (m, 1.4H, —CO$_2$—CH$_2$CH2-O—), 3.63 (m, 3.2H, —O—CH$_2$CH$_2$—O—), 2.30 (t, J=7.6 Hz, 1.9H, —CH$_2$CO$_2$—R), 2.24 (m, 3.8H, —CH$_2$CO$_2$—CH—R, —R$_1$), 1.98 (m, 2.2H, —CH(O$_2$C—R)—CH$_2$—CH═CH—CH$_2$—), 1.58 (m, 3.7H, —CH$_2$—CH$_2$—CO$_2$—R), 1.50 (m, 2.2H, —CH$_2$—CH—(O$_2$C—R)—CH$_2$—CH═CH—), 1.24 (m, 29.9H, —CH$_2$—) and 0.85 (i, J=6.7 Hz, 8.0H, —CH$_3$) ppm. $^{13}$C NMR (CDCl$_3$): δ 173.7 and 173.6 (R—CO$_2$—R$_1$), 173.4 (multiple signals, —R—CO$_2$—CH—R$_1$, —R$_2$), 133.4 (—CH(O$_2$C—R)—CH$_2$—HC═CH—), 124.3 (—CH(O$_2$C—R)—CH$_2$—HC═CH—), 73.6 (multiple signals, R$_1$—, R$_2$—HC—O$_2$C—R$_3$), 70.6-70.5 (multiple signals, —O—CH$_2$CH$_2$—O—), 69.2 and 69.1 (R—CO$_2$—CH$_2$C$_7$H$_2$—O—), 63.3 and 63.2 (R—CO$_2$—CH$_2$CH$_2$—O—), 34.6 (multiple signals, —CH$_2$—CO$_2$—R), 34.1 (multiple signals, —CH$_2$—CO$_2$—CH—R, —R$_1$), 33.6 (—CH$_2$—CH(O$_2$C—R)—CH$_2$—CH═CH—), 33.6 (—CH$_2$—CH—(O$_2$C—R)—CH$_2$—CH═CH—), 32.0-31.7 (multiple signals, —CH(O$_2$C—R)—CH$_2$—CH═CH—CH$_2$—), 29.6-29.1 (multiple signals, —CH$_2$—), 27.3 (multiple signals, —CH—(O$_2$C—R)—CH$_2$—CH═CH—CH$_2$—), 25.3-24.8 (multiple signals, —CH$_2$—CH$_2$—CO$_2$—R), 22.6-22.5 (multiple signals, R—CH$_2$—CH3), 14.1 and 14.0 (—CH$_2$—CH$_3$) ppm.

Laurate capped ricinoleate estolide polyethylene glycol-200 diester epoxide (LREE-PEG200-LREE) [10] (Scheme 3): Laurate capped ricinoleate estolide polyethylene glycol-200 diester (LRE-PEG200-LRE) (56.11 g, 0.0484 moles) was placed in a 1 L jacketed reactor with overhead stirrer, glass stopper, and condenser (no water flow through the condenser). The jacketed reactor was connected to a circulating bath maintained at 35° C. To the ester 50 mL of hexane was added followed by formic acid (1.90 mL, 0.0484 moles) and then 30% hydrogen peroxide (9.7 mL, 0.097 moles) and stirred at 35° C. while adding a second portion of 30% hydrogen peroxide (9.7 mL, 0.097 moles) after 2 h with the final portion of 30% hydrogen peroxide (4.8 mL, 0.048 moles) added after an additional 2 h. The reaction was allowed to stir at 35° C. for a total of 24 h from the first addition of hydrogen peroxide. The reaction was quenched by the addition of hexane (50 mL) and washing the organic layer in a separatory funnel 2×25 mL of pH 5 buffer (1.1 M NaH$_2$PO$_4$) and 1×25 mL of saturated sodium chloride solution. The solution was gravity filtered through a #54 Whatman filter paper and concentrated in vacuuo to yield 47.2 g (0.0402 moles) of a colorless epoxide oil (LREE-PEG200-LREE). $^1$H NMR (CDCl$_3$): δ 5.01 (m, 1.1H, R—, R$_1$—CH (O$_2$C—R$_2$)), 4.19 (m, 2.0H, —CO$_2$—CH$_2$CH$_2$—O—), 3.65 (m, 2.1H, —CO$_2$—CH$_2$CH$_2$—O—), 3.62 (m, 6.2H, —O—CH$_2$CH$_2$—O—), 2.92 (m, 1.3H, —CH(O$_2$CR)—CH$_2$—CH(O)CH—), 2.82 (m, 1.3H, —CH(O$_2$C—R)—CH$_2$—CH(O)CH—), 2.28 (m 6.0H, —CH$_2$CO$_2$—R and —CH$_2$CO$_2$—CH—R, —R$_1$) 1.78 and 1.69 (m, 3.0H, —CH (O$_2$C—R)—CH$_2$—CH═CH—CH$_2$—), 1.58 (m, 8.8H, —CH$_2$—CH$_2$—CO$_2$—R), 1.50-1.37 (m, 7.9H, —CH$_2$—CH—(O$_2$C—R)—CH$_2$—CH═CH—), 1.22 (m, 45.3H, —CH$_2$—) and 0.83 (t, J=7.0 Hz, 8.0H, —CH$_3$) ppm. $^{13}$C NMR (CDCl$_3$): δ 174.1 (R—CO$_2$—R$_1$), 173.7 and 173.3 (—RCO$_2$—CH—R$_1$, —R$_2$), 72.1-72.0 (R—, R$_2$—HC—O$_2$C—R$_3$), 70.6-70.5 (multiple signals, —O—CH$_2$CH$_2$—O—), 69.2-69.1 (R—CO$_2$—CH$_2$CH$_2$—O—), 63.3-61.6 (R—CO$_2$—C—H$_2$CH$_2$—O—), 56.7 and 56.1 (—CH (O$_2$C—R)—CH$_2$—CH(O)CH—), 53.9 and 53.6 (—CH (O$_2$CR)—CH$_2$—CH(O)CH—), 34.6 (—CH$_2$—CO$_2$—R), 34.1 (R—, R$_1$—CH—O$_2$C—CH$_2$—) 32.8 and 32.6 (—CH$_2$—CH—(O$_2$C—R)—CH$_2$—CH═CH— and —CH$_2$—CO$_2$—CH—R$_1$, —R$_2$), 33.6 (—CH$_2$—CH(O$_2$C—R)—CH$_2$—CH═CH—), 31.9-27.8 (multiple signals, —CH$_2$—), 25.3-24.8 (multiple signals, —CH$_2$—CH$_2$—CO$_2$—R), 22.6-22.5 (multiple signals, R—CH$_2$—CH$_3$), 14.1 and 14.0 (—CH$_2$—CH$_3$) ppm.

Laurate capped ricinoleate estolide polyethylene glycol-200 diester dihydroxy (LREDH-PEG200-LREDH) [11] (Scheme 3): Laurate capped ricinoleate estolide polyethylene glycol-200 diester epoxide (47.2 g, 0.0402 moles) was placed in a 500 mL round-bottom flask with magnetic stir bar and 50 mL of tetrahydrofuran (THF) added to dissolve the oil. Aqueous sulfuric acid (6M, 13.4 mL, 0.0805 moles) was added all at once and the reaction stirred at room temperature for 1 h. The reaction was transferred to a separatory funnel with 50 mL of hexane and washed with 3×50 mL of pH 5 buffer (1.1M NaH$_2$PO$_4$) and 1×50 mL with saturated sodium chloride solution. The hexane layer was removed in vacuuo and the oil gravity filtered through a #54 Whatman filter paper to yield 47.1 g of oil (LREDH-PEG200-LREDH). $^1$H NMR (CDCl$_3$): δ 5.01-4.80 (m, 1.2H, R—, R$_1$—CH(O$_2$C—R$_2$)), 4.19 (m, 1.3H, —CO$_2$—CH$_2$CH$_2$—O—), 3.92, 3.86, 3.80, 3.46, 3.25, 3.23 (m, 2.2H —CH—(OH)—CH(OH)—), 3.66 (m, 1.4H, —CO$_2$—CH$_2$CH$_2$—O—), 3.62 (m, 3.2H, R—O—CH$_2$CH$_2$—O—R), 2.29 (m 4.0H, —CH$_2$CO$_2$—R and —CH$_2$CO$_2$—CH—R$_1$, R$_2$), 1.72 (m, 1H, —CH(O$_2$C—R)—CH$_2$—CH(OH)—CH (OH)—), 1.58 (m, 6.7H, —CH$_2$—CH$_2$—CO$_2$—R), 1.42 (m, 4H, —CH$_2$—CH—(O$_2$C—R)—CH$_2$—CH(OH)—CH (OH)—CH$_2$—), 1.25 (m, 29.9H, —CH2-) and 0.85 (t, J=6.7 Hz, 5.9H, —CH$_3$) ppm. $^{13}$C NMR (CDCl$_3$): δ 173.9 (R—CO$_2$—R$_1$ and RCO$_2$—CH—R$_1$, R$_2$), 74.1 (—CH (O$_2$C—R)—CH$_2$—CH(OH)—CH(OH)—), 72.6 (R$_1$—, R$_2$—HC(O$_2$C)—R$_3$), 70.6 (multiple signals, R—O—CH$_2$CH$_2$—O—), 69.2 (R—CO$_2$—CH$_2$CH$_2$—O—), 63.3 (R—CO$_2$—CH$_2$CH$_2$—O—), 34.2 (—CH$_2$—CO$_2$—R), 34.2 (R—, R$_1$—CH—O$_2$C—CH$_2$—) 32.0-29.2 (multiple signals, —$CH_2$—), 25.89-24.6 (multiple signals, —$CH2$-$CH_2$—$CO_2$—R), 22.7 (multiple signals, R—$CH_2$—$CH_3$), 14.1 and 14.0 (—$CH_2$—$CH_3$) ppm.

12-Hydroxystearate estolide capped ricinoleate polyethylene glycol-200 diester dihydroxy (HSERDH-PEG200-HSERDH) [12] (Scheme 6): Methyl ricinoleate (10.0 g, 0.0321 moles) was placed in a 500 mL round-bottom flask equipped with a magnetic stir bar and vacuum adapter located in a heating mantle controlled by a temperature controller. Polyhydroxy stearate estolide (HSE) (69.0 g, 0.0321 moles, EN value of 4.34) was added to the flask followed by 1.0 mL (0.003 moles) of tin(II) octoate. The reaction was heated at 170° C. with stirring for 24 h then polyethylene glycol-200 (2.85 mL, 0.0161 moles) was added and continued to heat at 170° C. under vacuum for an additional 42 h. The reaction was cooled to room temperature, then added 120 mL of ethyl acetate, formic acid (0.6 mL, 0.0152 moles), followed by 30% hydrogen peroxide (3.0 mL, 0.030 moles), a condenser (under atmospheric pressure) was placed on the flask and warmed the reaction to 60° C. with stirring. After 2 h 30% hydrogen peroxide (3.0 mL, 0.030 moles) was added and continued heating at 60° C. After an additional 4 h, 30% hydrogen peroxide (1.6 mL, 0.016 moles) was added and continued heating at 60° C. for 7 days and the reaction was checked each day by NMR for consumption of the olefin and the presence of peroxide in the reaction mixture by KI test strip. After 7 days sulfuric acid (6M, 5 mL, 0.030 moles) was added and stirred at room temperature for 1 h then the reaction mixture was transferred into a separatory funnel with 100 mL of hexane and $Na_2HPO_4$ (0.5 M, 90 mL) followed by $Na_2S_2O_3$ (0.5M, 20 mL) and THF (20 mL to break the emulsion formed) were added. NMR indicated the reaction had only opened 73% of the epoxide, thus the oil was dissolved in THF (100 mL), sulfuric acid (6M, 5 mL, 0.03 moles) was added and stirred at room temperature for an additional 1 h. The same work up as previously described gave complete conversion of epoxide to dihydroxyl by NMR. $^1$HNMR ($CDCl_3$): δ 5.08-4.95 (m, 0.4H, R—, ($R_1$ containing dihydroxyl)-CH—($O_2C$—$R_2$)), 4.86 (m, 8.8H, R—, $R_1$—CH—($O_2C$—$R_2$)), 4.22 (m, 2.0H, —$CO_2$—$CH_2CH_2$—O—), 3.88, 3.83, 3.74, 3.49, 3.39, 3.26 (m, 3.5H, —CH—(OH)—CH(OH)—), 3.69 (m, 2.3H, —$CO_2$—$CH_2CH_2$—O—), 3.64 (m, 7.4H, —O—$CH_2CH_2$—O—), 3.58 (m, 0.4H, —$CH_2$—CH(OH)—$CH_2$—) 2.32 (m, 4.3H, —$CH_2CO_2$—R), 2.27 (t, 20.7H, J=7.4 Hz, —$CH_2CO_2$—CH—R, $R_1$), 1.61 (m, 30.7H, —$CH_2$—$CH_2$—$CO_2$—R), 1.46 (m, 47.4H, —CH2-CH—($O_2C$—R)—$CH_2$—CH(OH)—CH(OH)—$CH_2$— and —CH($O_2C$—$R_1$)—$CH_2$—CH(OH)—CH(OH)—), 1.25 (m, 276.9H, —$CH_2$—), and 0.87 (t, J=6.7 Hz, 38.9H, —$CH_3$) ppm. $^{13}$C NMR ($CDCl_3$): δ 173.7 (R—$CO_2$—$R_1$ and $RCO_2$—CH—$R_1$, $R_2$), 74.8 (—$CH_2$—CH(OH)—$CH_2$—), 74.0 ($R_1$—, $R_2$—HC—$O_2C$—$R_3$), 74.0, 73.0, 72.4, 72.0, 70.3 and 68.0 (—CH($O_2C$—R)—$CH_2$—CH(OH)—CH (OH)—), 70.6 and 70.5 (—O—$CH_2CH_2$—O—), 69.2 (R—$CO_2$—$CH_2CH_2$—O—), 63.3 (R—$CO_2$—($H_2CH_2$—O—), 35.0-33.5 (—$CH_2$—$CO_2$—R and R—, $R_1$—CH—$O_2C$—$CH_2$—) 31.9-28.9 (multiple signals, —$CH_2$—), 25.8-24.8 (multiple signals, —($H_2$—$CH_2$—$CO_2$—R), 22.7 (multiple signals, R—$CH_2$—$CH_3$), 14.1 and 14.0 (—$CH_2$—$CH_3$) ppm.

All the estolide derivatives shown in Table 3 (table 2) except LREDH-HEXDIOL-LREDH, OE-PEG400-OE and HSE-PEG400-HSE were synthesized by the methods reported by Isbell et al. 2018 and used without any further purification as reported therein. [best to leave in]Viscosity and viscosity index: Kinematic viscosities were measured using ASTM D445-97 using a calibrated Cannon-Fenske viscometer tube obtained from Cannon Instrument Co. (State College, Pa.). Measurements were conducted in a Temp-Trol viscosity bath obtained from Precision Scientific (Chicago, Ill.) at 40° C. and 100° C. Viscosity index was calculated using ASTM D2270-93 method. All measurements were run in triplicate. [best to leave in]12-Hydroxystearate estolide polyethylene glycol-400 diesters (HSE-PEG400-HSE): PEG-400 diesters were synthesized by placing the 12-hydroxystearate estolide (25 g, 17 mmoles) in a 100 mL 3-neck round-bottom flask fitted with a condenser capped with a vacuum port, glass stopper, temperature probe and magnetic stir bar. PEG-400 (3.0 mL, 8.5 mmoles) was added to the flask and warmed in a heating mantle maintained by a temperature controller to 200° C. under vacuum (2 kPa). After 24 h, the mixture was cooled to room temperature to yield the 12-hydroxystearate estolide PEG-400 diester with an acid value of 11.44 mg KOH/g oil. $^1$H NMR ($CDCl_3$): δ 4.87 (m, 5.0H, R—, $R_1$—CH—$O_2C$—$R_2$), 4.23 (t, J=4.7 Hz, 2.0H, —$CO_2$—$CH_2CH_2$—O—), 3.69 (t, J=4.7 Hz, 2.1H, —$CO_2$—$CH_2CH_2$—O—), 3.65 (m, 14.0H, R—O—$CH_2CH_2$—O—R), 3.59 (m, 0.8H, R—, $R_1$—CH—OH), 2.33 (m, 3.0H, —$CH_2CO_2$—R), 2.28 (t, J=7.4 Hz 10.1H, —$CH_2CO_2$—CH—, —$R_1$), 1.62 (m, 13.4H, —$CH_2$—$CH_2$—$CO_2$—R), 1.50 (m, 20.6H, —$CH_2$—CH—($O_2C$—R)—$CH_2$—), 1.28 (m, 150.7H, —$CH_2$—) and 0.88 (m, 20.0H, —$C_3$) ppm. $^{13}$C NMR ($CDCl_3$): δ 173.7 (R—$C_2$—R and —$RCO_2$—CH—$R_1$, $R_2$), 74.1 ($R_1$—, $R_2$—HC—$O_2C$—$R_3$), 72.0 (—CH—OH), 70.6-70.5 (multiple signals, R—O—$CH_2CH_2$—O—$R_1$), 69.2 (R—$CO_2$—$CH_2CH_2$—O—), 63.3 (R—$CO_2$—$CH_2CH_2$—O—), 37.5 (—$CH_2$—CH(OH)—$CH_2$—), 34.7 (—$CH_2$—$CO_2$—CH—R, —$R_2$), 34.7 (—$CH_2$—$CO_2$—R), 34.3 (—$CH_2$—CH—($O_2C$—R)—$CH_2$—), 31.9-29.2 (multiple signals, —$CH_2$—), 25.3-24.9 (multiple signals, —$CH_2$—$CH_2$—$CO_2$—R), 22.6-22.6 (multiple signals, R—$H_2$—$CH_3$) and 14.1 and 14.0 (—$CH_2$—$CH_3$) ppm.

Oleic estolide polyethylene glycol-400 diesters (OE-PEG400-OE): PEG diesters were synthesized by placing oleic estolide (25 g, 33.4 mmoles) in a 100 mL 3-neck round-bottom flask fitted with a condenser capped with a vacuum port, glass stopper, temperature probe and magnetic stir bar. PEG-400 (5.9 mL, 16.7 mmoles) was added to the flask and warmed to 200° C. under vacuum (~2 kPa). The reaction was removed from the heat after 24 h where NMR confirmed complete conversion to PEG-400 diesters. $^1$H NMR ($CDCl_3$): δ 5.36 (m, 1.4H, —HC=CH—), 4.84 (m, 1.4H, R—, $R_1$—CH—$O_2C$—$R_2$), 4.21 (m, 2.0H, —$CO_2$—$CH_2CH_2$—O—), 3.68 (m, 2.1H, —$CO_2$—$CH_2CH_2$—O—), 3.64 (m, 17.0H, R—O—$CH_2CH_2$—O—R), 2.30 (t, J=7.4 Hz, 2.2H, —$CH_2CO_2$—R), 2.26 (t, J=7.5 Hz, 3.2H, —$CH_2CO_2$—CH—R, —$R_1$), 2.00-1.95 (m, 3.2H, —$CH_2$—CH=CH—$CH_2$—), 1.60 (m, 5.6H, —$CH_2$—$CH_2$—$CO_2$—R), 1.49 (m, 6.1H, —$CH_2$—CH—($O_2C$—R)—$CH_2$—), 1.25 (m, 54.0H, —$CH_2$—) and 0.86 (t, J=4.3 Hz, 7.8H, —$CH_3$) ppm. $^{13}$C NMR ($CDCl_3$): δ 173.8 (—$RCO_2$—CH—$R_1$, $R_2$), 173.6 (R—$CO_2$—$R_1$), 130.4 (multiple signals, —HC=CH—), 74.0 (R—, $R_2$—HC—$O_2C$—$R_3$), 70.6-70.5 (multiple signals, R—O—$CH_2CH_2$—O—R), 69.2 (R—$CO_2$—$CH_2CH_2$—O—), 63.3 (R—$CO_2$—$CH_2CH_2$—O—), 34.7 (—$CH_2$—$CO_2$—R), 34.1 (—$CH_2$—$CO_2$—CH—$R_1$, —$R_2$), 32.6-31.7 (multiple signals, —$CH_2$—CH=CH—$CH_2$—), 29.7-29.0 (multiple signals, —$CH_2$—), 25.3-24.8 (multiple signals, —$CH_2$—$CH_2$—$CO_2$—R), 22.6-22.6 (multiple signals, R—$CH_2$—$CH_3$) and 14.08 and 14.04 (—$CH_2$—$CH_3$) ppm.

Laurate capped estolide hexane diol diesters (LRE-HEX-DIOL-LRE): Hexane diol diesters were synthesized by placing laurate capped estolide (34.1 g, 69.0 mmoles) and 1,6 hexane diol (4.1 g, 35.0 mmoles) in a 250 mL 3-neck round-bottom flask equipped with a magnetic stir bar, vacuum adapter and temperature probe. Tin (II) 2-ethylhexanoate (0.7 g, 2.0 mmoles) was added to the mixture and the flask warmed to 150° C. with a heating mantle controlled by a temperature controller. The reaction was stirred under vacuum at 150° C. for 24 h at which point the excess estolide was removed by Kügelrohr distillation at 230° C., 10 Pa to yield a residue of 29.8 g (0.029 moles) 84.0% isolated mass yield of product and 6.0 g of estolide distillate. $^1$H NMR (CDCl$_3$): δ 5.45 (m, 1H, —CH—(OH)—CH$_2$—HC=CH—), 5.32 (m, 1.1H, —CH—(OH)—CH$_2$—HC=CH—), 4.88 (q, J=5.9 Hz 1.0H, R—, R$_1$—CH—O$_2$C—R$_2$), 4.06 (t, J=6.7 Hz, 2.4H, —CO$_2$—CH$_2$CH$_2$—R$_3$), 2.27 (m, 6.7H, —CH$_2$CO$_2$—CH$_2$—R, —R$_1$, —CH—(OH)—CH$_2$—HC=CH—), 2.0 (m, 2.2H, —CH$_2$CH—(OH)—), 1.61 (m, 7.3H, —RCH$_2$CH$_2$CO$_2$, R$_1$—), 1.52 (m, 2.2H, —HC=CHCH$_2$—), 1.38 (m, 3.1H, —CO$_2$—CH$_2$CH$_2$—R$_3$), 1.27 (m, 37.8H, —CH2-) and 0.87 (t, J=6.1 Hz, 7.2H, —CH$_3$) ppm. $^{13}$C NMR (CDCl$_3$): δ 173.8 (—RCO$_2$—CH—R, R$_2$), 173.5 (R—C$_2$—R$_1$), 132.5 (—CH—(OH)—CH$_2$—HC=CH—), 124.3 (—CH—(OH)—CH$_2$—HC=CH—), 73.6 (R—HC—O$_2$C—R$_2$), 64.1 (R—CO$_2$—CH$_2$CH$_2$—), 34.6-25.4 (multiple signals, —CH$_2$—), and 14.1 and 14.0 (—CH$_2$—CH$_3$) ppm.

Admixtures: Admixtures of estolide diesters with petroleum oil base-stocks were made by placing 0.60 g of diester in a 20 mL glass scintillation vial followed by adding 11.40 g of base-stock oil to make a 5 wt % solution. The vial was capped and mixed vigorously at room temperature until all of the diester was soluble. LREDH-PEG200-LREDH, HSERDH-PEG200-HSERDH and LREDH-HEXDIOL-LREDH diesters had very limited solubility in the petroleum oils, therefore a saturated solution of each diol was made. LREDH-PEG200-LREDH-0.3 g was placed in a 20 mL scintillation vial with ~15 g of base oil to make a mixture of ~2 wt %. The mixture was placed in a heating block set at 100° C. and the mixture was vigorously mixed every few minutes for 1 h at which point the vial was removed. The sample was allowed to cool to room temperature where the insoluble LREDH-PEG200-LREDH was allowed to separate from the solution. After 16 h at room temperature, the supernatant liquid was decanted into a clean 20 mL scintillation vial and the concentration of the LREDH-PEG200-LREDH measured by HPLC by dissolving ~0.5 g (measured to 0.0001 g) of saturated admixtures to 5 mL in a volumetric flask. The samples were injected on the HPLC as described above and the concentration determined using the LREDH-PEG200-LREDH standard curve. HSERDH-PEG200-HSERDH and LREDH-HEXDIOL-LREDH saturated concentrations in the base oils were performed the same as LREDH-PEG200-LREDH described above except 5 wt % admixtures were made by dissolving ~0.8 g of diester in ~15 g of base oil and their saturated concentrations are shown in Table 2.

Results and Discussion: Three base materials were used for the synthesis of diesters; oleic estolide (OE [1]), 12-hydroxystearate estolide (HSE [2]), and laurate capped ricinoleate estolide (LRE [3]) along with the monomers, a by-product in the synthesis of the starting oleic estolide.

Oleic estolide [1] was synthesized by the method of Isbell and Kleiman (1994) using perchloric acid as the catalyst and provided an estolide number of 1.96 in 68.8% yield as depicted in Scheme 1. The estolide number (EN) is the number of estolide bonds within the molecule and is equal to the oligomer number of fatty acid moieties minus one (Isbell & Kleiman, 1994).

Polyethylene glycol (PEG) diesters were chosen due to their ready availability and low cost, in addition to our desire to incorporate a polar functionality at the center of the diester molecule. PEG-200 diols (PEG with average molecular weight of 200) were selected from the available PEG diols because it provided a reasonable polar functionality that was still a liquid at room temperature and had some degree of solubility within the estolide base materials. Larger PEG diols greater than 400 average molecular weight were solids at room temperature and difficult to solubilize in the estolide. Conversion to the OE-PEG200-OE diester [7] (Scheme 1) was performed at 200° C. under vacuum. Complete conversion to the diester was observed within 24 h when this reaction was run under equal stoichiometry of estolide to PEG-200. Excess PEG-200 would increase the rate of esterification for this second order reaction but would also result in formation of monoesters. The monoester (OE-PEG200-OH [5]) of OE [1] was also synthesized as a reference compound for spectral analysis. To obtain the monoesters, an excess of PEG-200 (4 equivalents to OE) followed by distillation to remove excess PEG-200 gave the monoester [5]. In addition, the monomer (mainly elaidic acid) a byproduct of the synthesis of oleic estolide was converted to both PEG monoester (M-PEG200-OH [4]) and PEG diester (M-PEG200-M [6]) as reference standards.

12-Hydroxystearic acid as supplied from the manufacturer already contained homo-oligomerized estolide but was further polymerized by heating 12-hydroxystearic acid under vacuum at 150° C. for 24 h to give a quantitative conversion to estolide (HSE [2]) with an EN of 4.34 as shown in Scheme 2. HSE-PEG200-HSE [8] diesters were synthesized separately by reacting the HSE with 0.5 equivalents of the respective diols at 150° C. for 24 h under vacuum as shown in Scheme 2.

The laurate capped ricinoleate estolide [3] was synthesized from methyl ricinoleate and lauric acid using a tin(II) octoate catalyst with an excess of lauric acid at 150° C. for 48 h as shown in Scheme 3. For the laurate capped ricinoleate estolide [3], we observed that a reaction time of 24 h or absence of tin catalyst failed to completely cap all of the hydroxyl moieties of methyl ricinoleate. Reaction times could be shortened with lower equivalents of lauric acid but homo-oligomerization of the ricinoleate was observed. The fastest reaction rates were observed with a 4 mole equivalent excess of lauric acid per mole of hydroxyl functionality for 24 h at 150° C. with a tin(II) octoate catalyst where the excess lauric acid was easily removed via Kügelrohr distillation to give the laurate capped estolide with an EN=1. Conversion to the PEG-200 diester [9] was accomplished by reacting the sample with 0.5 equivalents of PEG-200 diol and 5% w/w tin(II) octoate at 150° C. for 24 h as shown in Scheme 3.

The epoxide [10] was synthesized from the residual olefin of LRE-PEG200-LRE diester [9] (Scheme 3). An equal molar equivalent of formic acid to estolide was employed using a 2.5 mole equivalent excess of hydrogen peroxide with respect to the olefins of the diester. The hydrogen peroxide was added in 1 mole equivalent portions at time zero, 2 h and 4 h and then allowed to stir for a total of 24 h at 35° C. open to the atmosphere. Reactions were run in hexane since reactions without solvent gave reduced yields of epoxides and incomplete consumption of the olefin. When reactions were run in ethyl acetate, faster rates of reactions were observed but significant ring opening of the epoxide to the dihydroxyl [11] occurred. The epoxide could be isolated with a neutralization work-up method or converted in situ to the dihydroxyl with 6M $H_2SO_4$(aq), using 1 mole equivalent per mole of epoxide at room temperature for 1 h. In a similar fashion, the dihydroxyl [12] from the ring opened epoxide of 12-hydroxystearate estolide capped ricinoleate PEG-200 diester (HSERDH-PEG200-HSERDH) was synthesized in a multi-step one pot reaction starting from methyl ricinoleate. The self oligomerized 12-hydroxystearic acid was used to cap methyl ricinoleate using tin octoate as a catalyst at 150° C. After 24 h PEG-200 diol was added and the reaction continued at 150° C. for another 24 h at which point the reaction mixture was treated with hydrogen peroxide and formic acid in ethyl acetate at 60° C. to form the epoxide. The reaction to produce HSERDH-PEG200-HSERDH [12] proceeded much slower than the LREE-PEG200-LREE [11] epoxidation reaction, requiring 7 days to reach completion compared to 24 h, without being bound by theory, possibly due to the bulky size of the HSE group which reduced miscibility with water and access to the hydrogen peroxide. In addition, the epoxide was significantly ring opened under the reaction conditions over this long time period, thus residual epoxide was hydrolyzed with aqueous 6M sulfuric acid in 2 h to afford the corresponding dihydroxyl [12].

Figure 2:
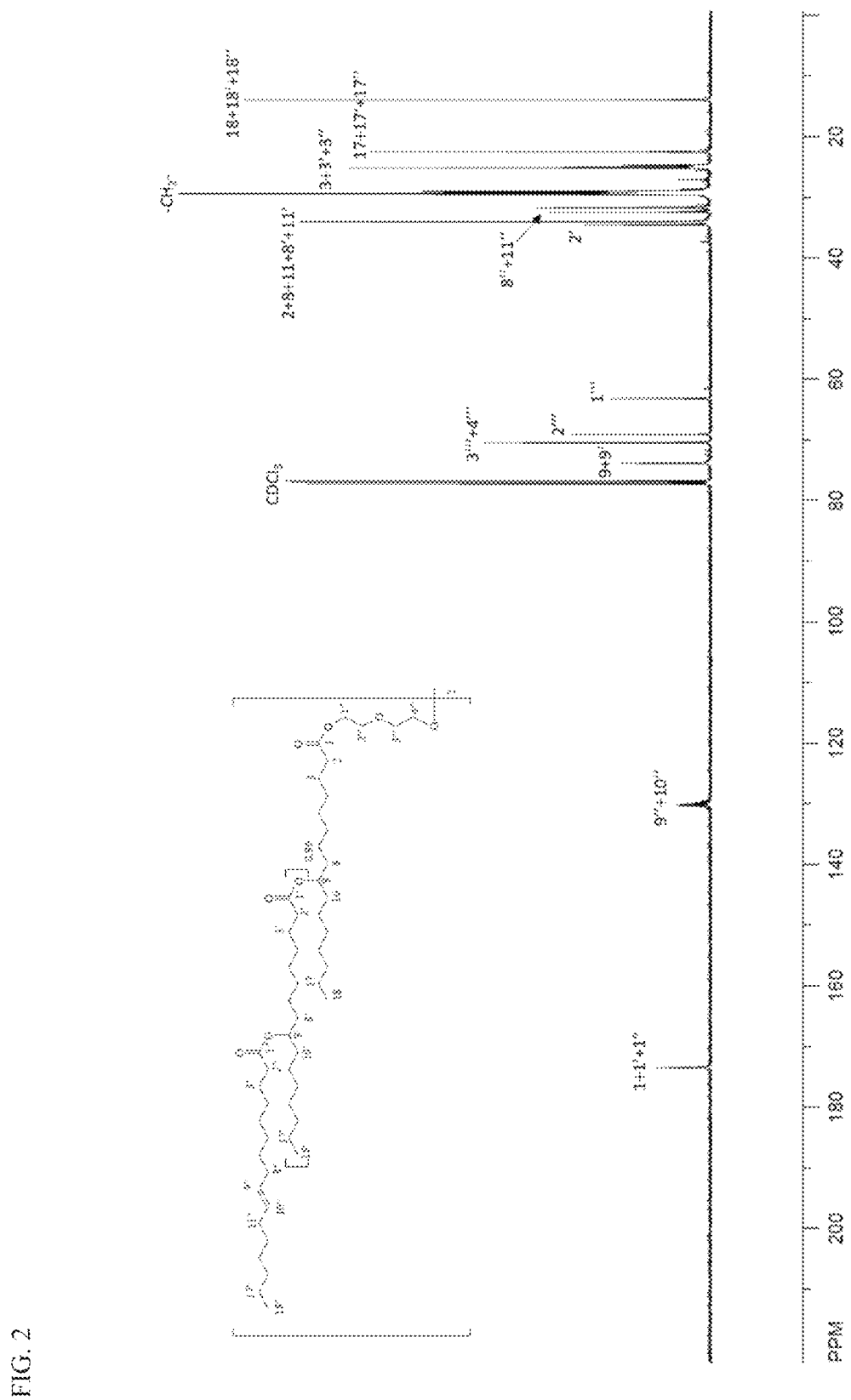
FIG. 2 shows $^{13}$C NMR of Oleic Estolide PEG-200 Diester (OE-PEG200-OE[7]) as described below.
Exemplary
Figure 3:
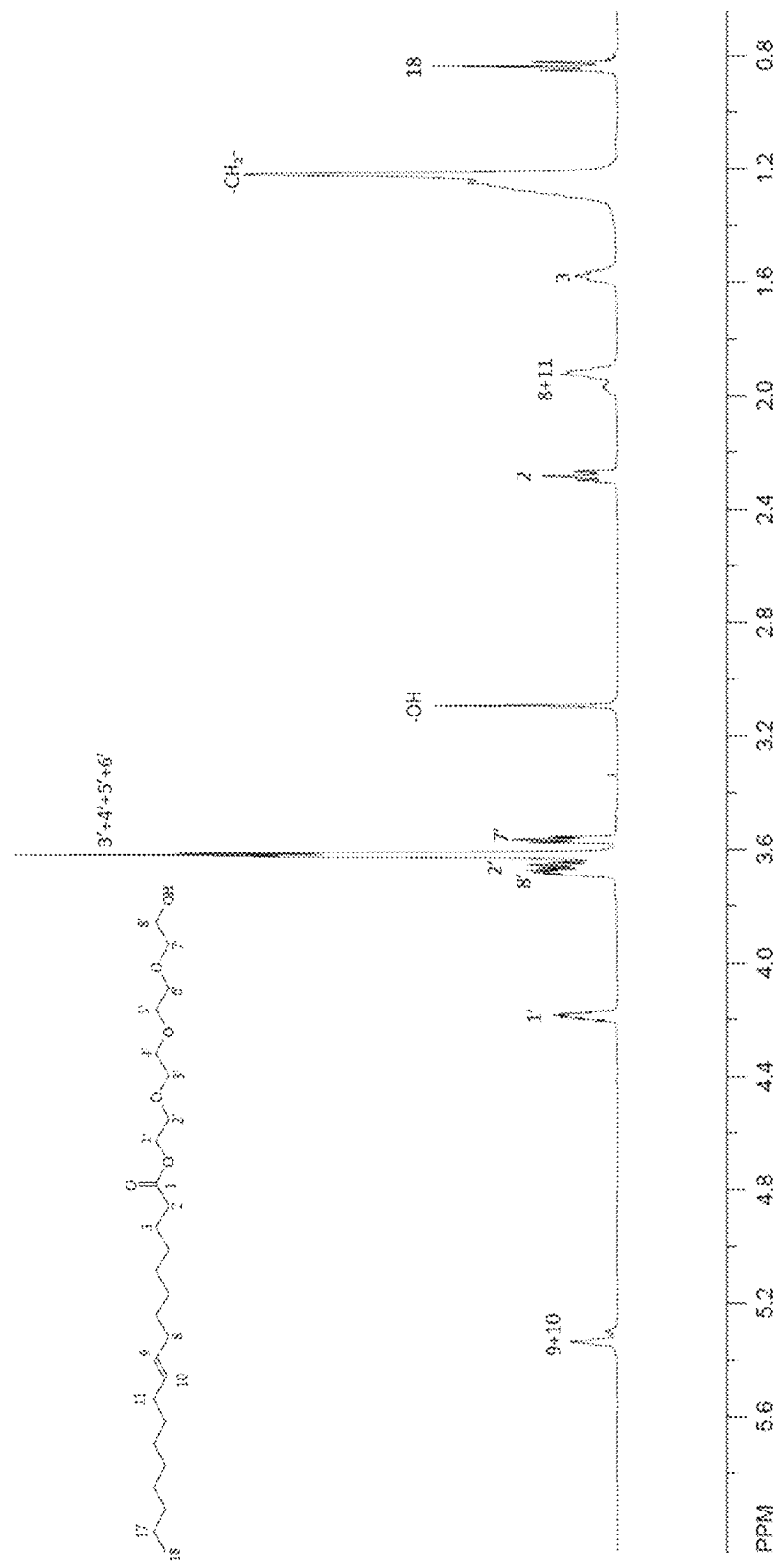
FIG. 3 shows $^1$H NMR of Monomer PEG-200 Monoester (M-PEG200-OH [4]) as described below.
Exemplary
Figure 4:
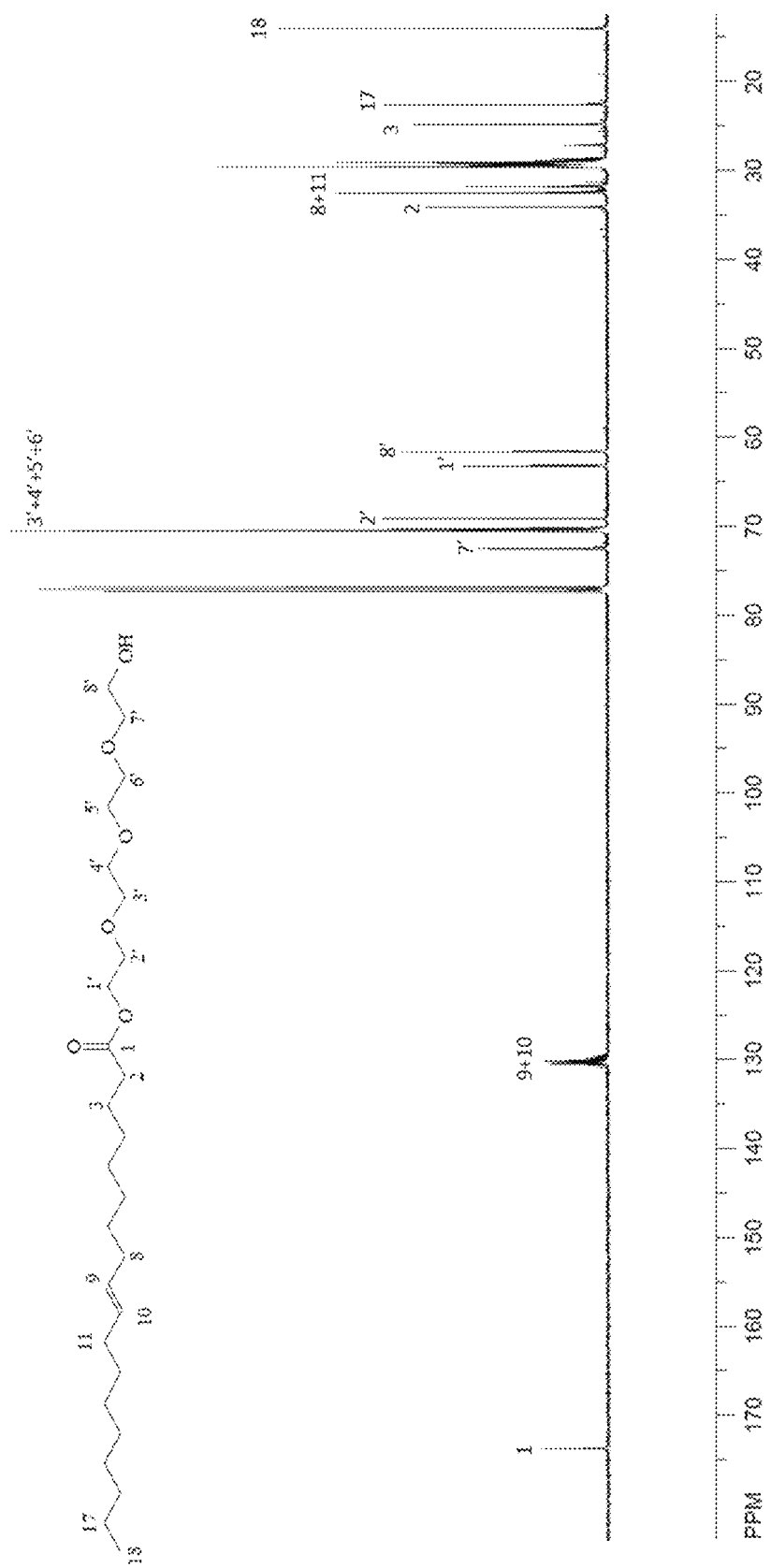
FIG. 4 shows $^{13}$C NMR of Monomer PEG-200 Monoester (M-PEG200-OH [4]) as described below.
Exemplary

All synthesized compounds were characterized by NMR spectroscopy using $^1H$, $^{13}C$, DEPT, HSQC, HMBC, and COSY experiments to make proton and carbon assignments. Oleic estolide PEG200 diester (OE-PEG200-OE [7]) had the estolide methine resonance of carbon 9 and 9' (FIG. 1 and FIG. 2) which appears at 4.85 ppm and 74.0 ppm in the proton and carbon spectra, respectively. These chemical shifts are in good agreement with reported resonance frequencies (Isbell & Kleiman 1994) for this estolide linkage and the HSQC spectrum shows that these two signals are coupled. The monomer polyethylene glycol-200 monoester [4] (FIG. 3) which was independently synthesized does not have this estolide methine signal, thus providing additional confirmation of the estolide linkage in OE-PEG200-OE [7]. The HMBC spectrum of OE-PEG200-OE indicated a multiple bond linkage between 4.85 ppm and carbon 1' at 173.4 ppm. In addition, proton signal intensity at positions 8" and 11" alpha to the olefin were diminished and a new signal for protons 8, 8' and 10, 10' of the alpha estolide 1.5-1.4 ppm are present in FIG. 1 compared to the oleate monoester in FIG. 3. The diester linkage to the OE-PEG200-OE [7] was observed at 4.2 ppm and 63.4 ppm which was confirmed by a coupling between these two signals in the HSQC. In addition, an HMBC coupling between the protons of 1" to carbon 1 was observed along with coupling to carbon 2". Importantly, the estolide methine to olefin integration ratio or estolide methine to protons on carbon 2 integration ratio remained constant from OE to OE-PEG200-OE indicating preservation of the estolide linkage and estolide number under the reaction conditions for formation of the diester. In an independent demonstration of the OE-PEG200-OE structural assignment, the OE-PEG200-OH [5] monoester was synthesized as well as the monomer PEG monoester (M-PEG200-OH [4]) and their spectral properties reported. FIG. 3 and FIG. 4 are the proton and carbon spectra of the M-PEG200-OH which had free PEG-OH functionality remaining. The monoester had additional PEG signals for the methylene of the free alcohol 7' and 8' at 3.60 and 3.70 ppm, respectively, in the proton and 72.5 and 61.6 ppm in the carbon which were absent in the diester of FIG. 1 and FIG. 2, thus confirming complete conversion of the OE into OE-PEG200-OE diesters. The HMBC confirmed the assignment of 7' and 8' of M-PEG-200-OH by indicating a coupling of protons on 8' (3.70 ppm) to carbon 7' at 72.5 ppm and 7' protons (3.60 ppm) coupled to 3'-6' carbons at 70.5 ppm and 8' carbon at 61.6 ppm.

The 12-hydroxystearic estolide PEG diester (HSE-PEG200-HSE [8]) provided very similar spectral analysis as the oleic estolide PEG200 diesters with two exceptions. First, HSE-PEG200-HSE did not contain any signals indicating olefins were present, compared to the signals from OE-PEG200-OE at 5.40 ppm and 130.0 ppm in the proton and carbon spectra, respectively. Second, the estolide methine integral was much larger due to the increased extent of the oligomerization of the HSE (EN=4.34) compared to OE (EN=1.96).

Figure 5:
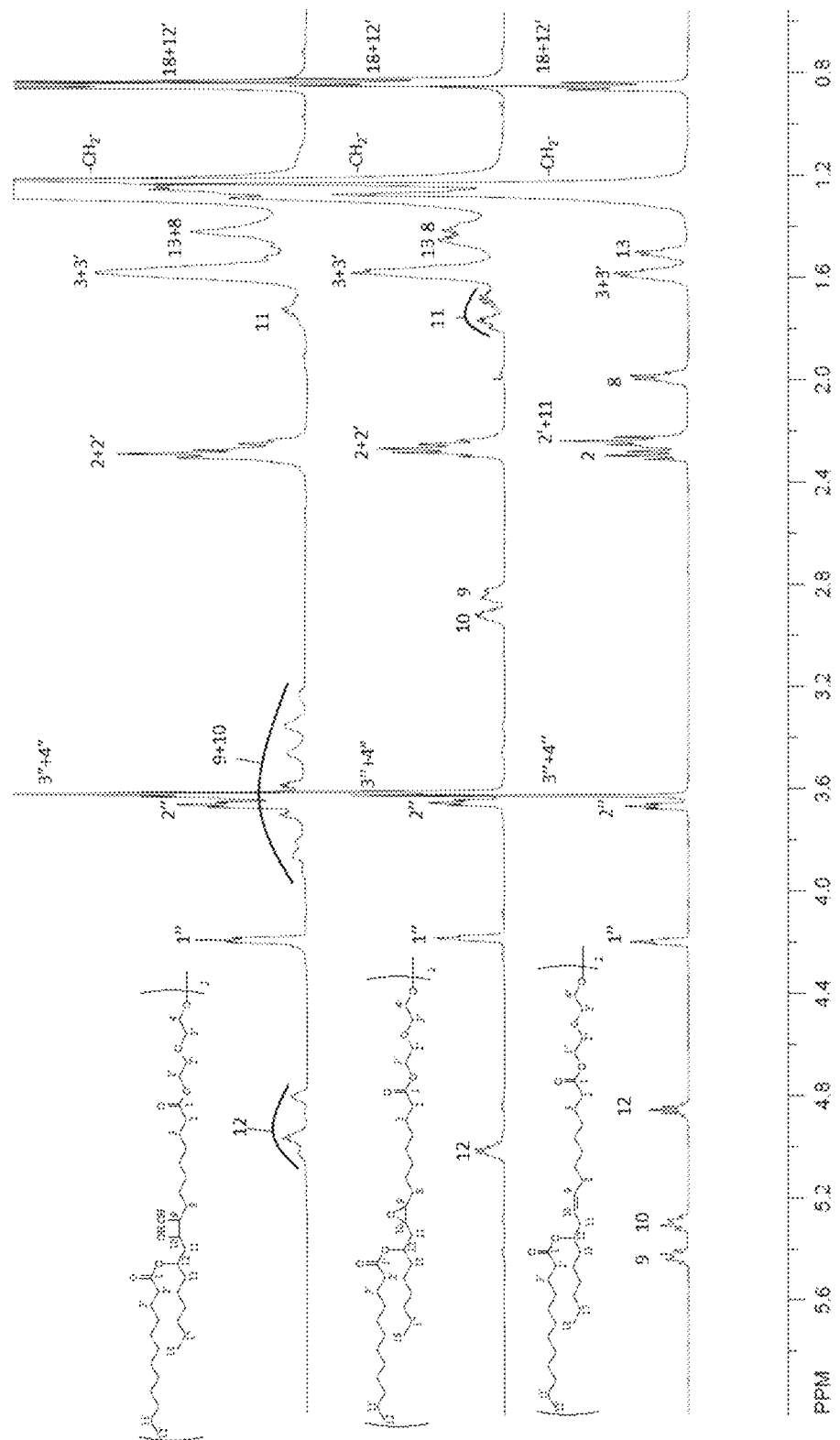
FIG. 5 shows $^1$H NMR Ricinoleate Estolide Compounds [9, 10, and 11] as described below.
Exemplary
Figure 6:
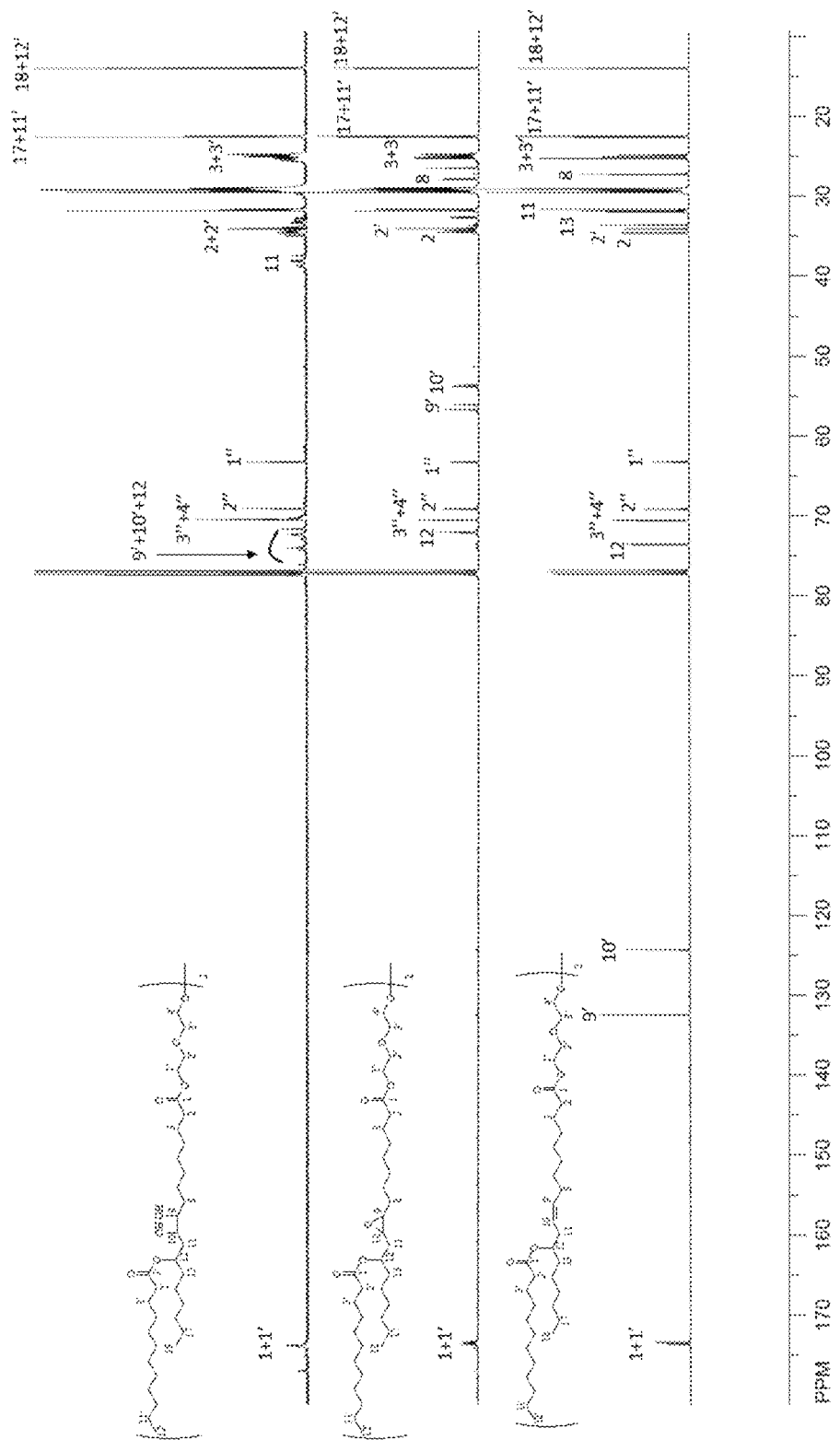
FIG. 6 shows $^{13}$C NMR Ricinoleate Estolide Compounds [9, 10, and 11] as described below.

FIG. 5 and FIG. 6 show stacked spectra that depicts the progression of the products detailed in Scheme 3 for laurate capped ricinoleate estolide PEG200 diester (LRE-PEG200-LRE [9]) to laurate capped ricinoleate estolide dihydroxy PEG200 diester (LREDH-PEG200-LREDH [11]). Three key points from these stacks were observed. First, the signature estolide methine signal was retained even though the synthetic scheme required the use of strong acids and in the presence of water that could hydrolyze the estolide. Second, the PEG diester was also unaffected by the reaction conditions. Third, the olefin was completely converted to epoxide [10] which was then ring opened to dihydroxyl [11]. The LRE-PEG200-LRE [9] estolide methine proton at 4.86 ppm and 73.6 ppm carbon spectra, respectively, underwent a downfield shift to 5.0 ppm in the proton and up field shift in the carbon to 72.1 ppm when the epoxide was formed beta to its location. This resonance shift was similar to what was reported by Doll et al. (2017) for estolides formed next to epoxides. When the epoxide was ring opened to the dihydroxyl, six diastereomers were formed and these resonances were observed between 5.1-4.75 ppm with the corresponding dihydroxy diastereomers resonances between 3.9-3.1 ppm. The cis epoxide protons were located at 2.85 and 2.93 ppm in the proton and 56.7 and 53.7 ppm in the carbon. Also, the alpha methyl protons on carbon 8 at 2.0 ppm moved to 1.35 ppm when the olefin was converted to the epoxide along with disappearance of the olefin protons at carbons 9 and 10, 5.43 and 5.30 ppm for the proton and 133.4 and 124.3 ppm in the carbon, respectively. The HSQC indicated coupling of the protons in all three spectra for carbon 12 to the carbon at 73 ppm in the starting olefin [9] and 72.4 ppm in the epoxide [10] but dispersed across a multiplet of carbons in the ring opened epoxide [11] 71-77 ppm. Table 1 details the long range two or three bond coupling in the HMBC spectrum between protons and carbons along with the proton-proton coupling between adjacent carbons for LREE-PEG200-LREE. Both of these two dimensional NMR methods aided in making structural assignments for all the synthesized molecules herein with LREE-PEG200-LREE via a COSY spectrum serving as the representative example for all structure assignments. The estolide protons at 5.0 ppm showed long range coupling in the HMBC to the carbonyl carbons at 173.4 ppm, carbon 3 at 25.5 ppm, carbon 10 of the epoxide at 54.1 ppm and carbon 11 at 33.4 ppm. The assignment of the protons of the epoxide showed HSQC coupling for carbon 10 protons at 2.92 ppm to the two carbon signals at 53.7 ppm and the carbon 9 protons of the epoxide at 2.84 ppm to the pair of carbons centered at 56.6 ppm. Long range HMBC and COSY coupling (Table 1) of carbon 10 protons was observed to carbon 11 at 32.5 ppm, the epoxide carbon 9, 56.6 ppm and only proton-carbon coupling to the estolide carbon 12 at 72.4 ppm. The epoxide carbon 9 was only coupled to carbon 8 at 27.6 ppm and carbon 10 at 53.7 ppm and demonstrated a proton-proton coupling to both those positions.

Three vegetable oil derived materials were used for the synthesis of diesters: oleic estolide (OE), 12-hydroxy stearate estolide (HSE), and laurate capped ricinoleate estolide (LRE).

The viscometric properties of all synthesized compounds were determined as both neat oils and as viscosity improvers in PAO and mineral base oils up to 5% w/w admixtures. The PAO series was 2 cSt, 4 cSt and 8 cSt oils which are commonly used in formulations of the multi-weight crankcase oils. The mineral base oil series that is commonly used in crankcase applications are 100N, 220N and 600N. Table 3 lists the viscosities of these neat oils at 40° C. and 100° C. with their respective VI calculated. The mineral base oil series has the lowest VI values of 104-108 as expected and the vegetable-based PEG diesters have the highest VI values of 111-205.

We examined the effect of oligomerization (estolides vs. monomers), the impact of molecular size (monoesters vs. diesters and estolide number), impact of additive polarity (PEG-200 vs. hexane diol esters), and the role of hydrogen bonding (hydroxy moieties vs. alkyl chains) on the overall thickening ability of the additives at all temperatures and the ability to thicken a base oil preferentially at higher temperature.

In the first group, underivatized monomer, which was recovered from the synthesis of oleic estolide and was composed mainly of octadecenoic acid trans olefins distributed mainly at the Δ9 and Δ10 positions, was examined for thickening properties of the petroleum base oils. The monomer as a neat oil had a good VI for all of its' derivatives (Table 3), but only provided ~5% thickening of 2 cSt PAO with a 5% w/w admixture, and the thickening was based solely on the viscosity of the monomer derivatives which had a higher viscosity than the 2 cSt PAO (Table 4). The M-PEG200-OH monoester with a free terminal hydroxy moiety had the lowest percent increase on 2 cSt PAO viscosity, even less than the underivatized monomer possibly (without being bound by theory) due to the higher polarity of this derivative which would have reduced Vander Wal interactions with the non-polar base oil. Tables 5-9 show that the monomer series started to act as a diluent when the viscosity of the base oil was a higher value than the neat viscosity of the monomer derivative, thus a reduction in the admixtures viscosity was observed commensurate with the concentration of the monomer in solution.

In the second group, oleic estolide was examined as a thickening agent and viscosity improver for petroleum base oils. First, the neat oleic estolides had significantly higher viscosities (19 cSt-57 cSt at 100° C.) compared to 1.7 cSt-12.9 cSt for the petroleum base oils (Table 3). Because of the higher viscosity of the oleic estolide derivatives, all of the admixtures except the OE-PEG200-OH were thickened at the 5% w/w concentration (Tables 4-9). The OE-PEG200-OH free alcohol acted as a diluent in the 600N mineral oil base stock at 40° C., even though its neat oil viscosity was higher than the 600N oil, but provided minimal thickening at 100° C. with a 2.3% increase in viscosity. In general, the oleic estolide series provided greater thickening at 40° C. rather than at 100° C., demonstrating no associative interactions within this derivative class other than those interactions with the bulk oil. The oleic estolide provided up to 18.5% increase in viscosity even with a 5% w/w admixture in 2 cSt PAO, with practically no effect in the 600N mineral oil where a 5.6% increase in viscosity was observed at 100° C. for the oleic estolide free acid and 5.1% and 5.2% increases for the OE-PEG200-OE and OE-PEG400-OE diesters, respectively, at this temperature. The higher molecular weight of the PEG400 diester compared to the PEG200 diester did not provide any significant additional thickening for all the OE admixtures examined. The monoester OE-PEG200-OH free alcohol provided no increase in viscosity at either temperature, similar to the M-PEG200-OH.

In the third group, hydroxy stearic estolide (HSE) was examined for its thickening properties. This group of estolides had a higher oligomer number with an estolide number (EN)=3.86 versus the EN=1.96 for OE. Due to the effect of the higher molecular weight, an overall increase in viscosity of the 5% admixtures in all base oils (Tables 3-9) was observed. In addition, the 40° C. viscosity was increased more than the 100° C. viscosity in most cases as would be expected from simply adding a higher molecular weight molecule to a mixture where its molecular volume remains unchanged throughout the temperature studied. The HSE-PEG200-HSE versus the HSE-PEG400-HSE admixtures gave similar viscosity increases for all the base oils but saw a dramatic increase in thickening for both of the viscous base oils, 8 cSt and 600N, where both the 40° C. and the 100° C. viscosity were dramatically increased for the longer PEG400 polyether chain (Tables 6 and 9). Furthermore, the HSE-PEG400-HSE increased viscosity more at 100° C. rather than at 40° C. in the 600N oil possibly (without being bound by theory) due to the higher polar nature of the molecule which would fold on itself at lower temperature where it had lower solubility in the 600N oil. As the temperature increased, solubility of the additive in the base oil also increased which allowed the bulky groups to interact, thereby enhancing its thickening properties at the higher temperature.

Building upon designing a more compact molecule at low temperature and opening a bulky molecule at high temperature, we postulated that a hydrogen bond site in the backbone of the estolide could help hold the molecule in a rigid compact structure at low temperature. Yet, when higher temperatures were present, the energy of solution would disrupt the intramolecular hydrogen bond and release the bulkiness of the molecule to increase solution viscosity. The laurate capped ricinoleate estolide provided the appropriate handle to test the effect of a hydrogen bond cross-linking group on the ability to minimize molecular volume at low temperature and maximize molecular volume at high temperature. As the series of estolide esters were examined, the methyl ester (LRE) provided the lowest increase in viscosity followed by the PEG200 diester (LRE-PEG200-LRE), but the thickening effect is similar for both of these derivatives which lack a hydrogen bond linkage as seen by the similar increase in viscosity at both 40° C. and 100° C. (Tables 4-9). The potential hydrogen bonded molecule synthesized by epoxidation and ring opening to the dihydroxy derivative of LRE-PEG200-LRE derivatized to LREDH-PEG200-LREDH reduced the solubility significantly over the other diester materials examined. Saturated solutions of all the base oils were made by mixing the base oil with a 2 w/w % of LREDH-PEG200-LREDH at 100° C. for 2 h then allowing to stand at room temperature for 24 h followed by decanting the supernatant oil away from the diester. Percent solubility was determined by HPLC where the diester was found to be 0.41-0.48% concentration range across all of the base oils and these values are reported in Table 2. These admixtures were then used to determine the thickening effect of LREDH-PEG200-LREDH. This dihydroxy diester provided greater thickening at 100° C. compared to 40° C. in all base oils except 100N. This data suggested that the potential to establish an intramolecular hydrogen bond may make the molecule more compact at lower temperature where the hydrogen bond was present. Furthermore, when the energy of the system exceeded the strength of the hydrogen bond the bulkiness of the molecule was released to provide additional thickening at the higher temperatures. To further explore the nature of this effect, we synthesized a diester lacking the large number of hydrogen bond sites of the PEG-200 and substituted a hexanediol linkage. When this linkage was employed in the LREDH-HEXDIOL-LREDH, the admixture viscosity was increased more at 40° C. compared to 100° C. The admixture viscosity data demonstrated the important role of the polarity of the PEG-200 polyether oxygens rather than the potential intramolecular hydrogen bond between the dihydroxy moieties on opposite sides of the diester. In addition, the underivatized LRE-PEG200-LRE diester provided greater viscosity increases in almost all the base oils at 100° C. compared to 40° C. and this molecule lacked the potential to hydrogen bond and confirmed the role of polarity from the PEG200 polyether oxygens as the critical factor that impacts solution viscosity. Therefore, associative interactions between molecules containing the PEG200 moiety appear to play a larger role to increase solution viscosity. Unfortunately, the solubility of the LREDH-PEG200-LREDH molecule was so low this effect only had a minimal impact on the overall viscosity of the solution where 100° C. viscosity was increased by <2%. In an effort to increase the solubility of the ricinoleate diesters and increase the bulk of the molecule, the PEG-200 ricinoleate was capped with hydroxy stearic estolide (HSE) then epoxidized and ring opened to the dihydroxy diester compounds (HSERDH-PEG200-HSERDH). The HSERDH-PEG200-HSERDH molecule was capped by an estolide with an EN=3.86 on each side of the PEG-200 diester. The additional alkyl chains increased the solubility of the dihydroxy derivate from ~0.45% to ~3.5% in the base oils. However, the HSERDH-PEG200-HSERDH, in general, increased the viscosity greater at the 40° C. temperature over the 100° C., demonstrating that the presence of the hydroxy moiety capable of hydrogen bonding had little to no effect on the solution viscosity, possibly (without being bound by theory) due to the large size of the molecule, making it difficult for a hydrogen bond to develop at any of the observed temperatures.

Conclusions: Estolides from oleic acid, methyl ricinoleate and 12-hydroxystearic acid were synthesized and converted to their PEG-200 diesters with surprisingly no loss of the estolide linkage in the formation of the diester. Monoesters were independently synthesized to demonstrate the absence of these potential side products in the reaction mixture and aid in the characterization of the complex diesters.

Stoichiometric equivalents of PEG-200 to estolide in the presence of tin octoate catalyst gave good conversion to diester with no monoester products when the reaction was allowed to go to completion. Epoxidation of the ricinoleate estolides was possible with a hydrogen peroxide and formic acid method without hydrolysis of the estolide or PEG ester linkages. Furthermore, ring opening of the epoxide by aqueous sulfuric acid did not hydrolyze the estolide linkage. All of the products were fully characterized by NMR spectroscopy including two dimensional methods that demonstrated multiple bond connections within the assigned structures.

PEG diesters of estolides surprisingly had a significant impact at increasing solution viscosity at 5% or less additive rates in synthetic and mineral oil base fluids increasing 100° C. viscosities up to 25.8% for a PAO 2 cSt oil. Higher oligomer estolides derived from 12-hydroxy stearic acid surprisingly provided the greatest increase in viscosity index where a 21% improvement in the 100N base oil was observed. The polarity of the diester linkage surprisingly also played a critical role in viscosity performance where a more polar polyether diester (PEG) gave greater improvement in viscosity index compared to an alkyl (hexane diol) linked diester where equivalent estolides LRE-PEG200-LRE versus LRE-HEXDIOL-LRE gave 13.9% and 0.0% viscosity index improvement, respectfully. A hydrogen bond capable moiety within the backbone of the estolide LREDH-PEG200-LREDH reduced the solubility of the additive in base oil considerably (<0.5%) and had less than 1% impact on viscosity index improvement.

All of the references cited herein, including U.S. patents and U.S. patent application Publications, are incorporated by reference in their entirety.

Thus, in view of the above, there is described (in part) the following:

A composition comprising (or consisting essentially of or consisting of) at least one member of the group consisting of (1) estolide polyethylene glycol diesters

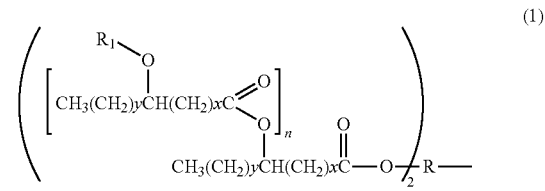

wherein x and y are each equal to 1 or greater than 1, wherein x+y=from 11 to 21;
wherein n is 0, 1, or greater than 1;
wherein R is a residual of a diol, wherein the diol may be any chain length of polyethylene glycol;
wherein R is a triol;
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;
wherein the predominant species of secondary ester linkage is at the 9 or 10 position, or secondary ester linkage is at the 11 or 12 position, or secondary ester linkage is at the 13 or 14 position, or secondary ester linkage is at the 5 or 6 position, or secondary ester linkage is at the 12 position, or secondary ester linkage is at the 14 position;

(2) hydroxy derived estolide polyethylene glycol diesters:

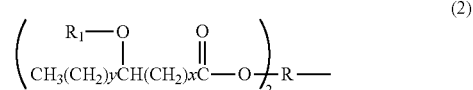

wherein x and y are each equal to 1 or greater than 1, wherein x+y=from 11 to 21;
wherein R is a residual of a diol, wherein the diol may be any chain length of polyethylene glycol (—$CH_2$—O—);
wherein R is a residual of a triol;

wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;

wherein the predominant species of secondary ester linkage is at the 9 or 10 position, or secondary ester linkage is at the 11 or 12 position, or secondary ester linkage is at the 13 or 14 position, or secondary ester linkage is at the 5 or 6 position, or secondary ester linkage is at the 12 position, or secondary ester linkage is at the 14 position;

(3) unsaturated hydroxy derived estolide polyethylene glycol diesters:

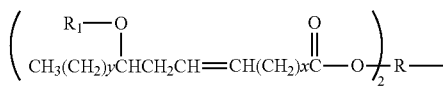

wherein x and y are each equal to 1 or greater than 1, wherein x+y=from 8 to 18;

wherein R is a residual of a diol, wherein the diol may be any chain length of polyethylene glycol (—$CH_2$—O—);

wherein R is a residual of a triol;

wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;

wherein the predominant species of secondary ester linkage is at the 9 or 10 position, or secondary ester linkage is at the 11 or 12 position, or secondary ester linkage is at the 13 or 14 position, or secondary ester linkage is at the 12 position, or secondary ester linkage is at the 14 position;

(4) estolide trimetholpropane diesters:

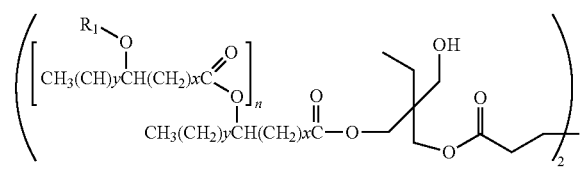

wherein x and y are each equal to 1 or greater than 1; wherein x+y=from 11 to 21;

wherein n is 0, 1, or greater than 1;

wherein R1 is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;

wherein the predominant species of secondary ester linkage is at the 9 or 10 position, or secondary ester linkage is at the 11 or 12 position, or secondary ester linkage is at the 13 or 14 position, or secondary ester linkage is at the 5 or 6 position, or secondary ester linkage is at the 12 position, or secondary ester linkage is at the 14 position;

(5) hydroxy derived estolide trimetholpropane diesters:

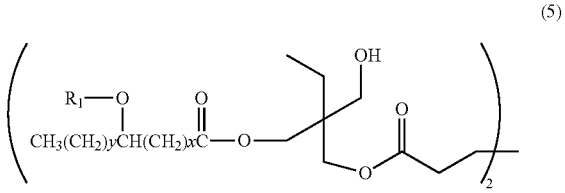

wherein x and y are each equal to 1 or greater than 1, wherein x+y=from 11 to 21;

wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;

wherein the predominant species of secondary ester linkage is at the 9 or 10 position, or secondary ester linkage is at the 11 or 12 position, or secondary ester linkage is at the 13 or 14 position, or secondary ester linkage is at the 5 or 6 position, or secondary ester linkage is at the 12 position, or secondary ester linkage is at the 14 position;

(6) unsaturated hydroxy derived estolide trimetholpropane diesters:

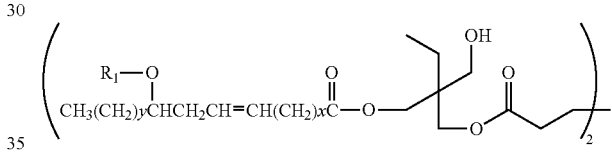

wherein x and y are each equal to 1 or greater than 1, wherein x+y=from 8 to 18;

wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;

wherein the predominant species of secondary ester linkage is at the 9 or 10 position, or secondary ester linkage is at the 11 or 12 position, or secondary ester linkage is at the 13 or 14 position, or secondary ester linkage is at the 12 position, or secondary ester linkage is at the 14 position;

(7) estolide epoxide polyethylene glycol diesters:

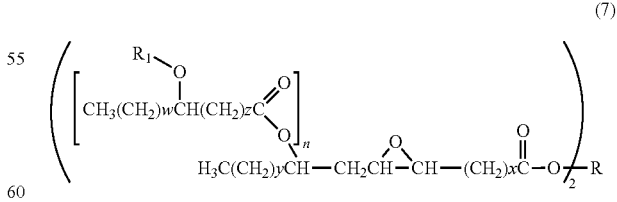

wherein x and y are each equal to 1 or greater than 1, wherein x+y=from 8 to 18;

wherein x and y are each equal to 1 or greater than 1, wherein w+z=from 11 to 21;

wherein the predominant species of secondary ester linkage is at the 12 or 14 position, wherein n is 0, 1, or greater than 1;
wherein R is a residual of a diol, wherein the diol may be any chain length of polyethylene glycol (—CH2-O—);
wherein R is a triol;
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;

(8) estolide dihydroxide polyethylene glycol diesters:

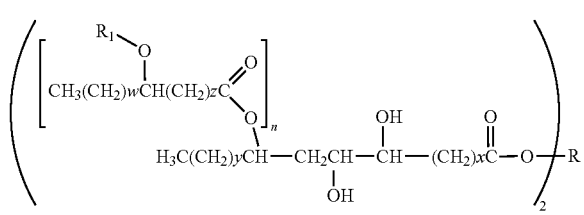

(8)

wherein x and y are each equal to 1 or greater than 1, wherein x+y=from 8 to 18;
wherein x and y are each equal to 1 or greater than 1, wherein w+z=from 11 to 21;
wherein the predominant species of secondary ester linkage is at the 12 or 14 position,
wherein n is 0, 1, or greater than 1;
wherein R is a residual of a diol, wherein the diol may be any chain length of polyethylene glycol (—CH2-O—);
wherein R is a triol;
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain:

(9) mono-capped hydroxy derived estolide epoxide polyethylene glycol diesters:

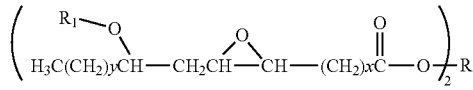

(9)

wherein x and y are each equal to 1 or greater than 1, wherein x+y=from 8 to 18;
wherein the predominant species of secondary ester linkage is at the 12 or 14 position,
wherein R is a residual of a diol, wherein the diol is any chain length of polyethylene glycol (—CH2-O—);
wherein R is a triol;
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;
wherein the predominant species of secondary ester linkage is at the 9 or 10 position, or secondary ester linkage is at the 11 or 12 position, or secondary ester linkage is at the 13 or 14 position, or secondary ester linkage is at the 5 or 6 position or secondary ester linkage is at the 12 position, or secondary ester linkage is at the 14 position;

(10) mono-capped hydroxy derived estolide dihydroxide polyethylene glycol diesters:

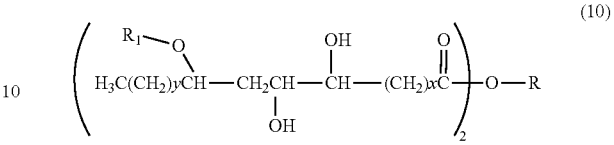

(10)

wherein x and y are each equal to 1 or greater than 1, wherein x+y=from 8 to 18;
wherein the predominant species of secondary ester linkage is at the 12 or 14 position,
wherein R is a residual of a diol, wherein the diol is any chain length of polyethylene glycol (—CH2-O—);
wherein R is a triol;
wherein $R_1$ is independently selected from hydrogen and a C1 to C36 fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;
and mixtures thereof; and optionally a carrier.

The above composition, wherein said composition comprises (or consists essentially of or consists of) at least one member of the group consisting of unsaturated hydroxy derived estolide polyethylene glycol diesters, hydroxy derived estolide trimetholpropane diesters, and mixtures thereof; and optionally a carrier.

The composition, wherein said composition comprises (or consists essentially of or consists of) unsaturated hydroxy derived estolide polyethylene glycol diesters and optionally a carrier.

The above composition, wherein said composition comprises (or consists essentially of or consists of) hydroxy derived estolide trimetholpropane diesters and optionally a carrier.

The composition according to claim 1, wherein said composition further comprises a lubricant.

A method to improve the viscosity index of a lubricant (e.g., mineral or polyalphaolefin (synthetic) base oils), said method comprising (or consisting essentially of or consisting of) mixing the composition according to claim 1 with a lubricant.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The invention illustratively disclosed herein suitably may be practiced in the absence of any element (e.g., method (or process) steps or composition components) which is not specifically disclosed herein. Thus, the specification includes disclosure by silence ("Negative Limitations In Patent Claims," AIPLA Quarterly Journal, Tom Brody, 41(1): 46-47 (2013): " . . . Written support for a negative limitation may also be argued through the absence of the excluded element in the specification, known as disclosure by silence . . . Silence in the specification may be used to establish written description support for a negative limitation. As an example, in Ex parte Lin [No. 2009-0486, at 2, 6 (B.P.A.I. May 7, 2009)] the negative limitation was added by amendment . . . In other words, the inventor argued an example that passively complied with the requirements of the negative limitation . . . was sufficient to provide support . . . This case shows that written description support for a negative limitation can be found by one or more disclosures of an embodiment that obeys what is required by the negative limitation . . . ."

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Observed Coupling for Laurate Capped Ricinoleate Estolide Epoxide PEG-200 Diester (LREE-PEG-200-LREE [10]) in 2-D HMBC and COSY NMR Spectra

| Chemical Shift $^{13}$C | $^1$H Position | NA 1 | 2.33-2.19 2 | 1.65-1.53 3 | 1.44-1.37 8 | 2.89-2.80 9 | 2.97-2.89 10 | 1.83-1.65 11 | 5.00-4.94 12 | NA 11 | 0.84 18 | 4.19 1" | 3.66 2" | 3.62 3"-4" | 1.36-1.16 —CH$_2$— |
|---|---|---|---|---|---|---|---|---|---|---|---|---|---|---|---|
| 173.6-173.4 | 1 | | L | L | | | | L | | | L | | L | | L |
| 34.6-33.6 | 2 | L | | L C | | | | | | | | | | | |
| 25.3-24.7 | 3 | | L C | | | | | L C | | | | | | | |
| 27.9-27.8 | 8 | | | | | L C | | | | | | | | | |
| 56.7 56.1 | 9 | | | | L C | | L C | LC | | | | | | | |
| 53.9 53.6 | 10 | | | | L | L C | | L | L | | | | | | |
| 32.5-35.0 | 11 | | | | | | L C | | L C | | | | | | |
| 72.0 | 12 | | | | | | L | LC | | | | | | | |
| 22.6-22.5 | 17 | | | | | | | | | | L | | | | L |
| 14.0 | 18 | | | | | | | | | L | | | | | LC |
| 63.3 | 1" | | | | | | | | | | | LC | | | |
| 69.1 | 2" | | | | | | | | | | | L C | | LC | |
| 70.5 | 3"-4" | | | | | | | | | | | | L C | | |
| 29.6-29.0 | —CH$_2$— | | L | L C | | | | | L C | | | | | | |

Chemical Shift is in ppm, L = Long range Proton-Carbon coupling (2 and 3 bonds) in HMBC and C = Proton-Proton coupling in COSY.
Refer to FIG. 5 and FIG. 6.

TABLE 2

Concentration of Saturated Solutions of Dihydroxy Derivatives in Base Oils

| Base Oil | LREDH-PEG200-LREDH % | HSERDH-PEG200-HSERDH % | LREDH-HEXDIOL-LREDH % |
|---|---|---|---|
| PAO 2cSt | 0.48$^a$ | 3.13$^a$ | 2.63$^a$ |
| PAO 4cSt | 0.42$^b$ | 3.11$^a$ | 3.05$^a$ |
| PAO 8cSt | 0.41$^c$ | 4.02$^b$ | 2.74$^a$ |
| 100N | 0.46$^{ad}$ | 3.52$^c$ | 2.31$^a$ |
| 220N | 0.44$^{ad}$ | 4.02$^b$ | 2.01$^b$ |
| 600N | 0.48$^a$ | 3.85$^b$ | 1.84$^c$ |

The means with the same letters within a column are not significantly different.

TABLE 3

Viscosities of Neat Base Oils and Additives

| Additives | 40° C. | 100° C. | VI |
|---|---|---|---|
| Monomer | 23.07$^a$ | 5.259$^a$ | 171 |
| M-PEG200-M | 34.37$^b$ | 7.732$^b$ | 205 |
| M-PEG200-OH | 31.72$^c$ | 6.288$^c$ | 153 |
| Oleic Estolide | 279.2$^d$ | 29.70$^d$ | 143 |
| OE-PEG200-OE | 460.1$^e$ | 57.20$^e$ | 194 |
| OE-PEG-200-OH | 141.4$^f$ | 19.14$^f$ | 154 |
| OE-PEG400-OE | 327.0$^g$ | 41.34$^g$ | 181 |
| HSE | ND | 48.48$^h$ | ND |
| HSE-PEG-200-HSE | 928.6$^h$ | 98.57$^i$ | 199 |
| HSE-PEG400-HSE | 963.7$^i$ | 103.2$^j$ | 203 |
| Ricinoleic Acid | 249.2$^j$ | 25.37$^k$ | 130 |

TABLE 3-continued

Viscosities of Neat Base Oils and Additives

| Additives | 40° C. | 100° C. | VI |
|---|---|---|---|
| LRE-Methyl Ester | 20.05$^k$ | 4.822$^l$ | 174 |
| LRE-PEG200-LRE | 84.71$^l$ | 15.53$^m$ | 196 |
| LREDH-PEG200-LREDH | 2521.9$^m$ | 103.9$^n$ | 111 |
| LREDH-HEXDIOL-LREDH | 636.6$^n$ | 31.25$^d$ | 71 |
| PAO 2cSt | 5.175$^o$ | 1.735$^o$ | NA |
| PAO 4cSt | 17.02$^p$ | 3.891$^p$ | 124 |
| PAO 8cSt | 46.66$^q$ | 7.802$^q$ | 136 |
| 100N | 19.81$^r$ | 4.114$^r$ | 108 |
| 220N | 43.07$^s$ | 6.580$^s$ | 104 |
| 600N | 105.9$^t$ | 12.19$^t$ | 106 |

All values in the 40° C. column are significantly different. Within the column means without letters in common differ significantly.

TABLE 4

Viscosities of 5% Additive in PAO 2cSt Base Oil

| Additives | 40° C. | % Change | 100° C. | % Change | VI |
|---|---|---|---|---|---|
| Monomer | 5.513$^a$ | 6.5 | 11.825$^a$ | 5.2 | NA |
| M-PEG200-M | 5.509$^a$ | 6.5 | 1.867$^b$ | 7.6 | NA |
| M-PEG200-OH | 5.416$^{ab}$ | 4.7 | 1.798$^c$ | 3.6 | NA |
| Oleic Estolide | 6.139$^e$ | 18.6 | 1.965$^d$ | 13.3 | NA |
| OE-PEG-200-OE | 6.130$^e$ | 18.5 | 2.025$^e$ | 16.7 | 131 |
| OE-PEG200-OH | 5.822$^d$ | 12.5 | 1.888$^f$ | 8.8 | NA |
| OE-PEG400-OE | 5.984$^e$ | 15.6 | 1.995$^g$ | 15.0 | NA |
| HSE | 6.684$^f$ | 29.2 | 2.146$^h$ | 23.7 | 130 |
| HSE-PEG200-HSE | 6.625$^f$ | 28.0 | 2.163$^{hi}$ | 24.7 | 141 |
| HSE-PEG400-HSE | 6.646$^f$ | 28.4 | 2.182$^i$ | 25.8 | 146 |
| Ricinoleic Acid | 5.980$^e$ | 15.6 | 1.948$^g$ | 12.3 | NA |
| LRE-Methyl Ester | 5.352$^b$ | 3.4 | 1.820$^a$ | 4.9 | NA |
| LRE-PEG200-LRE | 5.725$^d$ | 10.6 | 1.916$^k$ | 10.4 | NA |
| LREDH-PEG200-LREDH | 5.202$^g$ | 0.5 | 1.754$^l$ | 1.1 | NA |
| LREDH-HEXDIOL-LREDH | 5.450$^{ab}$ | 5.6 | 1.824$^a$ | 5.6 | NA |

TABLE 4-continued

Viscosities of 5% Additive in PAO 2cSt Base Oil

| Additives | 40° C. | % Change | 100° C. | % Change | VI |
|---|---|---|---|---|---|
| *HSERDH-PEG200-HSERDH* | *6.268$^h$* | *21.1* | *2.057$^m$* | *18.5* | *131* |

Bold is 0.48% w/w mixture
Bold italics is 2.63% w/w mixture
Italics indicate 3.13% w/w mixture
Within the column means without letters in common differ significantly

TABLE 5

Viscosities of 5% Additive in PAO 4cSt Base Oil

| Additives | 40° C. | % Change | 100° C. | % Change | VI | % Change |
|---|---|---|---|---|---|---|
| Monomer | 17.07$^a$ | 0.3 | 3.921$^a$ | 0.8 | 127 | 2.4 |
| M-PEG200-M | 17.20$^b$ | 1.1 | 3.975$^b$ | 2.2 | 131 | 5.6 |
| M-PEG200-OH | 17.13$^{bc}$ | 0.6 | 3.876$^c$ | −0.4 | 121 | −2.4 |
| Oleic Estolide | 19.37$^d$ | 13.8 | 4.309$^d$ | 10.7 | 133 | 7.3 |
| OE-PEG200-OE | 19.04$^e$ | 11.9 | 4.368$^e$ | 12.3 | 143 | 15.3 |
| OE-PEG200-OH | 18.65$^f$ | 9.6 | 4.102$^f$ | 5.4 | 122 | −1.6 |
| OE-PEG400-OE | 19.11$^e$ | 12.3 | 4.331$^g$ | 11.3 | 139 | 12.1 |
| HSE | 20.69$^g$ | 21.6 | 4.359$^e$ | 12.0 | 120 | −3.2 |
| HSE-PEG200-HSE | 20.38$^b$ | 19.7 | 4.547$^h$ | 16.9 | 142 | 14.5 |
| HSE-PEG400-HSE | 20.56$^g$ | 20.8 | 4.589$^i$ | 17.9 | 144 | 16.1 |
| Ricinoleic Acid | 20.57$^g$ | 20.9 | 4.201$^j$ | 8.0 | 107 | −13.7 |
| LRE-Methyl Ester | 16.92$^i$ | −0.5 | 3.946$^k$ | 1.4 | 132 | 6.5 |
| LRE-PEG200-LRE | 18.07$^j$ | 6.2 | 4.203$^j$ | 8.0 | 141 | 13.7 |
| LREDH-PEG200-LREDH | 17.01$^{ai}$ | −0.1 | 3.965$^{bk}$ | 1.9 | 133 | 7.3 |
| *LREDH-HEXDIOL-LREDH* | *17.40$^k$* | *4.4* | *4.018$^{bk}$* | *2.0* | *132* | *6.4* |
| *HSERDH-PEG200-HSERDH* | *18.99$^e$* | *11.6* | *4.318$^{dg}$* | *10.9* | *139* | *12.1* |

Bold is 0.42% w/w mixture
Bold italics is 3.05% w/w mixture
Italics indicate 3.11% w/w mixture
Within the column means without letters in common differ significantly

TABLE 6

Viscosities of 5% Additive in PAO 8cSt Base Oil

| Additives | 40° C. | % Change | 100° C. | % Change | VI | % Change |
|---|---|---|---|---|---|---|
| Monomer | 43.73$^a$ | −6.3 | 7.530$^a$ | −3.5 | 139 | 2.7 |
| M-PEG200-M | 44.09$^b$ | −5.5 | 7.727$^b$ | −1.0 | 145 | 6.6 |
| M-PEG200-OH | 44.72$^c$ | −4.2 | 7.504$^c$ | −3.8 | 134 | −1.5 |
| Oleic Estolide | 50.60$^d$ | 8.4 | 8.302$^d$ | 6.4 | 138 | 1.5 |
| OE-PEG200-OE | 50.89$^e$ | 9.1 | 8.409$^e$ | 7.8 | 140 | 2.9 |
| OE-PEG200-OH | 46.69$^f$ | 0.1 | 8.122$^f$ | 4.1 | 148 | 8.8 |
| OE-PEG400-OE | 49.60$^g$ | 6.3 | 8.331$^g$ | 6.8 | 143 | 5.1 |
| HSE | 49.69$^g$ | 6.5 | 8.295$^d$ | 6.3 | 141 | 3.7 |
| HSE-PEG200-HSE | 48.92$^h$ | 4.8 | 8.223$^h$ | 5.4 | 142 | 4.4 |
| HSE-PEG400-HSE | 53.80$^h$ | 15.3 | 8.636$^h$ | 10.7 | 137 | 0.7 |
| Ricinoleic Acid | 48.37$^i$ | 3.7 | 8.095$^i$ | 3.8 | 140 | 2.9 |
| LRE-Methyl Ester | 43.79$^a$ | −6.2 | 7.632$^j$ | −2.2 | 143 | 5.1 |
| LRE-PEG200-LRE | 47.04$^j$ | 0.8 | 8.081$^i$ | 3.5 | 145 | 6.6 |
| LREDH-PEG200-LREDH | 46.42$^k$ | −0.5 | 7.892$^k$ | 1.1 | 141 | 3.7 |
| *LREDH-HEXDIOL-LREDH* | *46.66$^l$* | *4.9* | *7.842$^l$* | *−4.7* | *138* | *1.5* |
| *HSERDH-PEG200-HSERDH* | *49.69g* | *6.5* | *8.455m* | *8.4* | *146* | *7.4* |

Bold is 0.41% w/w mixture
Bold italics is 2.74% w/w mixture
Italics indicate 4.02% w/w mixture
Within the column means without letters in common differ significantly

TABLE 7

Viscosities of 5% Additive in 100N Base Oil

| Additives | 40° C. | % Change | 100° C. | % Change | VI | % Change |
|---|---|---|---|---|---|---|
| Monomer | 20.12$^{ab}$ | 1.4 | 4.172$^a$ | 1.1 | 110 | 1.9 |
| M-PEG200-M | 20.23$^a$ | −0.9 | 4.241$^b$ | 2.8 | 115 | 6.5 |
| M-PEG200-OH | 20.07$^b$ | −1.7 | 4.105$^c$ | −0.5 | 104 | −3.7 |
| Oleic Estolide | 23.14$^c$ | 13.4 | 4.561$^d$ | 10.5 | 111 | 2.8 |
| OE-PEG200-OE | 23.19$^c$ | 13.6 | 4.692$^e$ | 13.7 | 122 | 13.0 |
| OE-PEG200-OH | 21.44$^d$ | 5.0 | 4.343$^f$ | 5.3 | 110 | 1.9 |
| OE-PEG400-OE | 23.16$^c$ | 13.5 | 4.668$^g$ | 13.1 | 120 | 11.1 |
| HSE | 24.02$^e$ | 17.7 | 4.908$^h$ | 19.0 | 131 | 21.3 |
| HSE-PEG200-HSE | 23.96$^e$ | 17.4 | 4.806$^i$ | 16.5 | 123 | 13.9 |
| HSE-PEG400-HSE | 25.61$^f$ | 25.5 | 4.820$^j$ | 16.8 | 109 | 0.9 |
| Ricinoleic Acid | 22.52$^g$ | 10.3 | 4.479$^j$ | 8.6 | 111 | 2.8 |
| LRE-Methyl Ester | 20.19$^{ab}$ | 1.9 | 4.133$^k$ | 4.6 | 105 | −2.8 |
| LRE-PEG200-LRE | 21.14$^h$ | 6.7 | 4.451$^l$ | 8.2 | 123 | 13.9 |
| LREDH-PEG200-LREDH | 20.22$^a$ | 2.1 | 4.174$^a$ | 1.5 | 109 | 0.9 |
| *LREDH-HEXDIOL-LREDH* | *20.90$^j$* | *4.4* | *4.247$^b$* | *2.0* | *108* | *0.0* |
| *HSERDH-PEG200-HSERDH* | *23.96e* | *20.9* | *4.809i* | *16.9* | *124* | *14.8* |

Bold is 0.46% w/w mixture
Bold italics is 2.31% w/w mixture
Italics indicate 3.52% w/w mixture
Within the column means without letters in common differ significantly

TABLE 8

Viscosities of 5% Additive in 220N Base Oil

| Additives | 40° C. | % Change | 100° C. | % Change | VI | % Change |
|---|---|---|---|---|---|---|
| Monomer | 40.15$^a$ | −6.8 | 6.408$^a$ | −2.6 | 109 | 4.8 |
| M-PEG200-M | 40.49$^b$ | −6.0 | 6.486$^b$ | −1.4 | 111 | 6.7 |
| M-PEG200-OH | 40.92$^c$ | −5.0 | 6.344$^c$ | −3.6 | 103 | −1.0 |
| Oleic Estolide | 46.83$^d$ | 8.7 | 7.136$^d$ | 8.4 | 111 | 6.7 |
| OE-PEG200-OE | 47.70$^e$ | 10.7 | 7.191$^e$ | 9.3 | 110 | 5.8 |
| OE-PEG200-OH | 43.98$^f$ | 2.1 | 6.775$^f$ | 3.0 | 108 | 3.8 |
| OE-PEG400-OE | 46.59$^g$ | 8.2 | 7.396$^g$ | 12.4 | 122 | 17.3 |
| HSE | 48.85$^h$ | 13.4 | 7.158$^h$ | 8.8 | 105 | 1.0 |
| HSE-PEG200-HSE | 50.97$^i$ | 18.3 | 7.477$^i$ | 13.6 | 109 | 4.8 |
| HSE-PEG400-HSE | 50.54$^j$ | 17.3 | 7.788$^j$ | 18.4 | 121 | 16.3 |
| Ricinoleic Acid | 45.22$^k$ | 5.0 | 6.91$^k$ | 5.0 | 109 | 4.8 |
| LRE-Methyl Ester | 39.71$^l$ | −7.8 | 6.399$^a$ | −2.7 | 111 | 6.7 |
| LRE-PEG200-LRE | 43.21$^m$ | 0.3 | 6.991$^l$ | 6.2 | 120 | 15.4 |
| LREDH-PEG200-LREDH | 42.57$^n$ | −1.2 | 6.638$^m$ | 0.9 | 108 | 3.8 |
| *LREDH-HEXDIOL-LREDH* | *42.96$^o$* | *2.1* | *6.645$^m$* | *1.0* | *107* | *2.9* |
| *HSERDH-PEG200-HSERDH* | *55.16p* | *28.1* | *7.606n* | *15.6* | *100* | *−3.8* |

Bold is 0.44% w/w mixture
Bold italics is 2.01% w/w mixture
Italics indicate 4.02% w/w mixture
Within the column means without letters in common differ significantly

TABLE 9

Viscosities of 5% Additive in 600N Base Oil

| Additives | 40° C. | % Change | 100° C. | % Change | VI | % Change |
|---|---|---|---|---|---|---|
| Monomer | 93.18$^a$ | −12.0 | 11.49$^a$ | −5.7 | 112 | 5.7 |
| M-PEG200-M | 92.91$^b$ | −12.3 | 11.62$^b$ | −4.7 | 114 | 7.5 |
| M-PEG200-OH | 96.44$^c$ | −8.9 | 11.43$^c$ | −6.2 | 106 | 0.0 |
| Oleic Estolide | 109.8$^d$ | 3.7 | 12.87$^d$ | 5.6 | 111 | 4.7 |
| OE-PEG200-OE | 112.4$^d$ | 6.1 | 12.81$^{eg}$ | 5.1 | 107 | 0.9 |
| OE-PEG200-OH | 103.9$^e$ | −1.9 | 12.28$^f$ | 0.7 | 110 | 3.8 |
| OE-PEG400-OE | 108.1$^f$ | 2.1 | 12.82$^g$ | 5.2 | 113 | 6.6 |
| HSE | 111.9$^g$ | 5.7 | 12.61$^h$ | 3.4 | 105 | −0.9 |
| HSE-PEG200-HSE | 107.6$^h$ | 1.6 | 12.79$^i$ | 4.9 | 113 | 6.6 |
| HSE-PEG400-HSE | 118.2$^i$ | 11.6 | 14.08$^j$ | 15.5 | 119 | 12.3 |
| Ricinoleic Acid | 106.9$^j$ | 0.9 | 12.47$^k$ | 2.3 | 109 | 2.8 |

TABLE 9-continued

Viscosities of 5% Additive in 600N Base Oil

| Additives | 40° C. | % Change | 100° C. | % Change | VI | % Change |
|---|---|---|---|---|---|---|
| LRE-Methyl Ester | 92.55[k] | −12.6 | 11.53[l] | −5.4 | 113 | 6.6 |
| LRE-PEG200-LRE | 99.87[l] | −2.9 | 12.26[f] | 0.6 | 115 | 8.5 |
| LREDH-PEG200-LREDH | 104.0[e] | −1.8 | 12.28[f] | 0.7 | 110 | 3.8 |
| *LREDH-HEXDIOL-LREDH* | *103.4[m]* | *0.5* | *11.96[m]* | *−2.4* | *105* | *−0.9* |
| *HSERDH-PEG200-HSERDH* | *115.8[n]* | *9.3* | *13.88[n]* | *13.9* | *119* | *12.3* |

Bold is 0.48% w/w mixture
Bold italics is 1.84% w/w mixture
Italics indicate 3.85% w/w mixture
Within the column means without letters in common differ significantly

We claim:

1. A composition comprising at least one member of the group consisting of (1) estolide polyethylene glycol diesters:

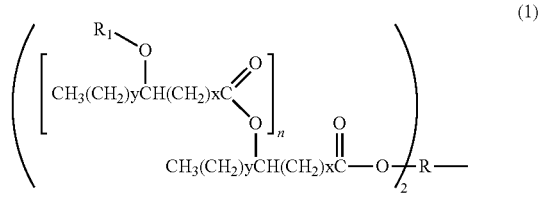

(1)

wherein x and y are each equal to 1 or greater than 1, wherein x+y=from 11 to 21;
wherein n is 0, 1, or greater than 1;
wherein R is a residue of a diol, wherein the diol is any chain length of polyethylene glycol;
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;
wherein the predominant species of secondary ester linkage is at the 9 or 10 position, or secondary ester linkage is at the 11 or 12 position, or secondary ester linkage is at the 13 or 14 position, or secondary ester linkage is at the 5 or 6 position, or secondary ester linkage is at the 12 position, or secondary ester linkage is at the 14 position;
wherein compound (1) meets at least one of the following conditions: x is not 10, y is not 5, n is not zero, n is not greater than 1, and $R_1$ is not hydrogen or a hydroxy-substituted stearic ester;

(2) hydroxy derived estolide polyethylene glycol diesters:

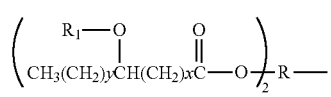

(2)

wherein x and y are each equal to 1 or greater than 1, wherein x+y=from 11 to 21;
wherein R is a residue of a diol, wherein the diol is any chain length of polyethylene glycol (—$CH_2$—$CH_2$—O—);
wherein $R_1$ is independently selected from $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain, wherein $R_1$ is not hydrogen;
wherein the predominant species of secondary ester linkage is at the 9 or 10 position, or secondary ester linkage is at the 11 or 12 position, or secondary ester linkage is at the 13 or 14 position, or secondary ester linkage is at the 5 or 6 position, or secondary ester linkage is at the 12 position, or secondary ester linkage is at the 14 position;

(3) unsaturated hydroxy derived estolide polyethylene glycol diesters:

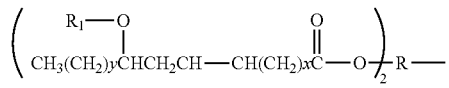

wherein x and y are each equal to 1 or greater than 1, wherein x+y=from 8 to 18;
wherein R is a residue of a diol, wherein the diol is any chain length of polyethylene glycol (—$CH_2$—$CH_2$—O—);
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;
wherein the predominant species of secondary ester linkage is at the 9 or 10 position, or secondary ester linkage is at the 11 or 12 position, or secondary ester linkage is at the 13 or 14 position, or secondary ester linkage is at the 12 position, or secondary ester linkage is at the 14 position;
wherein compound (3) meets at least one of the following conditions: $R_1$ is not hydrogen, x is not 7, and y is not 5;

(4) bridged estolide trimethylolpropane diesters:

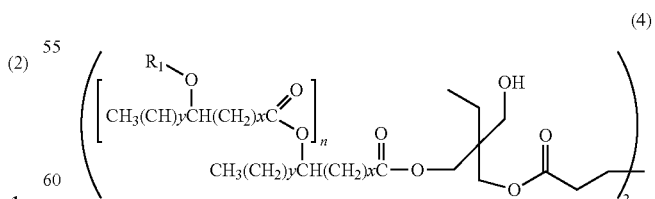

(4)

wherein x and y are each equal to 1 or greater than 1;
wherein x+y=from 11 to 21;
wherein n is 0, 1, or greater than 1;
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;

wherein the predominant species of secondary ester linkage is at the 9 or 10 position, or secondary ester linkage is at the 11 or 12 position, or secondary ester linkage is at the 13 or 14 position, or secondary ester linkage is at the 5 or 6 position, or secondary ester linkage is at the 12 position, or secondary ester linkage is at the 14 position;

(5) bridged hydroxy derived estolide trimethylolpropane diesters:

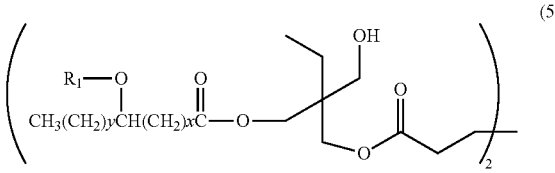

(5)

wherein x and y are each equal to 1 or greater than 1, wherein x+y=from 11 to 21;

wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;

wherein the predominant species of secondary ester linkage is at the 9 or 10 position, or secondary ester linkage is at the 11 or 12 position, or secondary ester linkage is at the 13 or 14 position, or secondary ester linkage is at the 5 or 6 position, or secondary ester linkage is at the 12 position, or secondary ester linkage is at the 14 position;

(6) bridged unsaturated hydroxy derived estolide trimethylolpropane diesters:

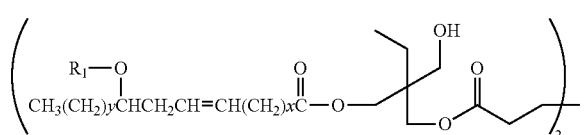

wherein x and y are each equal to 1 or greater than 1, wherein x+y=from 8 to 18;

wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;

wherein the predominant species of secondary ester linkage is at the 9 or 10 position, or secondary ester linkage is at the 11 or 12 position, or secondary ester linkage is at the 13 or 14 position, or secondary ester linkage is at the 12 position, or secondary ester linkage is at the 14 position;

(7) estolide epoxide polyethylene glycol diesters:

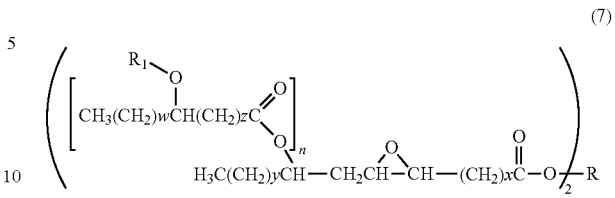

(7)

wherein x and y are each equal to 1 or greater than 1, wherein x+y=from 8 to 18;
wherein x and y are each equal to 1 or greater than 1, wherein w+z=from 11 to 21;
wherein the predominant species of secondary ester linkage is at the 12 or 14 position,
wherein n is 0, 1, or greater than 1;
wherein R is a residue of a diol, wherein the diol is any chain length of polyethylene glycol (—CH$_2$—CH$_2$—O—);
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;

(8) estolide dihydroxide polyethylene glycol diesters:

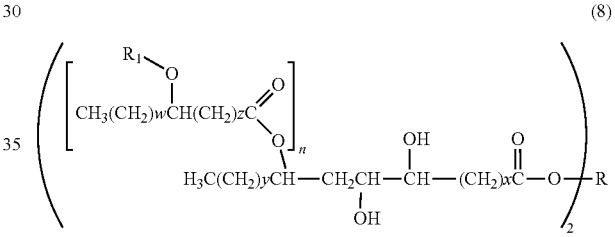

(8)

wherein x and y are each equal to 1 or greater than 1, wherein x+y=from 8 to 18;
wherein x and y are each equal to 1 or greater than 1, wherein w+z=from 11 to 21;
wherein the predominant species of secondary ester linkage is at the 12 or 14 position,
wherein n is 0, 1, or greater than 1;
wherein R is a residue of a diol, wherein the diol is any chain length of polyethylene glycol (—CH$_2$—CH$_2$—O—);
wherein $R_1$ is independently selected from hydrogen and a $C_1$ to $C_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;

(9) mono-capped hydroxy derived estolide epoxide polyethylene glycol diesters:

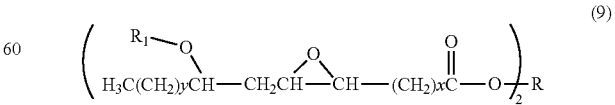

(9)

wherein x and y are each equal to 1 or greater than 1, wherein x+y=from 8 to 18;
wherein the predominant species of secondary ester linkage is at the 12 or 14 position, wherein R is a residue of a diol, wherein the diol is any chain length of polyethylene glycol (—CH$_2$—CH$_2$—O—);
wherein R$_1$ is independently selected from hydrogen and a C$_1$ to C$_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;
wherein the predominant species of secondary ester linkage is at the 9 or 10 position, or secondary ester linkage is at the 11 or 12 position, or secondary ester linkage is at the 13 or 14 position, or secondary ester linkage is at the 5 or 6 position or secondary ester linkage is at the 12 position, or secondary ester linkage is at the 14 position;

(10) mono-capped hydroxy derived estolide dihydroxide polyethylene glycol diesters:

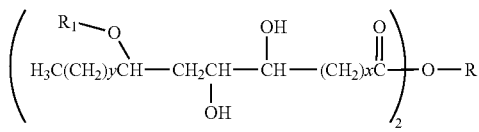

(10)

wherein x and y are each equal to 1 or greater than 1, wherein x+y=from 8 to 18;
wherein the predominant species of secondary ester linkage is at the 12 or 14 position,
wherein R is a residue of a diol, wherein the diol is any chain length of polyethylene glycol (—CH$_2$—CH$_2$—O—);
wherein R$_1$ is independently selected from hydrogen and a C$_1$ to C$_{36}$ fatty ester which may be saturated or unsaturated, branched or straight chain, and substituted or unsubstituted, or a residual fragment of oleic, ricinoleic, lesquerolic, stearic, lauric, capric, palmitic, myristic or other fatty acid chain;
and mixtures thereof; and optionally a carrier.

2. The composition according to claim 1, wherein said composition comprises at least one member of the group consisting of unsaturated hydroxy derived estolide polyethylene glycol diesters, bridged hydroxy derived estolide trimethylolpropane diesters, and mixtures thereof; and optionally a carrier.

3. The composition according to claim 1, wherein said composition comprises unsaturated hydroxy derived estolide polyethylene glycol diesters and optionally a carrier.

4. The composition according to claim 1, wherein said composition comprises bridged hydroxy derived estolide trimethylolpropane diesters and optionally a carrier.

5. The composition according to claim 1, wherein said composition further comprises a lubricant.

6. A method to improve the viscosity index of a lubricant, said method comprising mixing the composition according to claim 1 with a lubricant.

* * * * *